(12) United States Patent
Leban et al.

(10) Patent No.: US 6,235,717 B1
(45) Date of Patent: May 22, 2001

(54) PHARMACEUTICAL COMPOUNDS

(75) Inventors: Johann Jakob Leban; Douglas Byron Sherman; James Frederick Sigafoos, all of Durham; Andreas Spaltenstein, Raleigh; Osvaldo Humberto Viveros, Chapel Hill, all of NC (US); David Chi-cheong Wan, Shatin (HK)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 08/481,365

(22) PCT Filed: Jan. 4, 1994

(86) PCT No.: PCT/GB94/00009

§ 371 Date: Jul. 3, 1995

§ 102(e) Date: Jul. 3, 1995

(87) PCT Pub. No.: WO94/15956

PCT Pub. Date: Jul. 21, 1994

(30) Foreign Application Priority Data

Jan. 4, 1993 (GB) ................................................ 9300048

(51) Int. Cl.$^7$ ................................................. C07K 5/08
(52) U.S. Cl. .......................................... 514/18; 530/331
(58) Field of Search ........................ 530/331; 514/18, 514/2

(56) References Cited

U.S. PATENT DOCUMENTS

| | | | | |
|---|---|---|---|---|
| 5,382,569 | * | 1/1995 | Cody | 514/17 |
| 5,444,042 | * | 8/1995 | Bartus | 514/2 |
| 5,498,728 | * | 3/1996 | Sohda | 548/493 |
| 5,504,070 | * | 4/1996 | Bihovsky et al. | 514/15 |
| 5,607,831 | * | 3/1997 | Henkart | 435/5 |
| 5,650,508 | * | 7/1997 | Powers | 544/168 |
| 5,663,296 | * | 9/1997 | Doherty | 530/331 |
| 5,693,617 | * | 12/1997 | Stein | 514/18 |

FOREIGN PATENT DOCUMENTS

| | | |
|---|---|---|
| 0342541 | 11/1989 | (EP) . |
| 0460679 | 12/1991 | (EP) . |
| 0472077 | 2/1992 | (EP) . |
| 0518299 | 12/1992 | (EP) . |

OTHER PUBLICATIONS

Fagny et al., Peptides 12(4):773–778, 1991.*
Morrison, Organic Chemistry, Fourth Edition , pp. 1122–1123, 1983.*
Pliura, Biochem J. 759–762, 1992.*
Taguchi, Biochem Biophys Res. Comm. 185 pp. 1133–40, 1992.*

* cited by examiner

Primary Examiner—Christopher S. F. Low
Assistant Examiner—David Lukton
(74) Attorney, Agent, or Firm—Nixon & Vanderhye P.C.

(57) ABSTRACT

The present invention provides a compound of formula (I) or a salt thereof

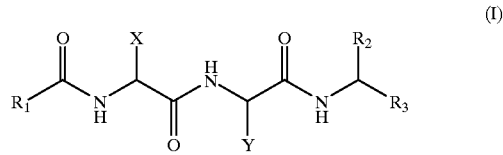

as well as methods of making and using same.

17 Claims, No Drawings

PHARMACEUTICAL COMPOUNDS

This application is the US National stage of PCT/GB94/00009, filed Jan. 4, 1994.

The present invention relates to compounds which show inhibition of endothelin converting enzyme (ECE), to pharmaceutical compositions containing such compounds and to their use in animal and human medicine.

Endothelins (ETs) are highly homologous 21 amino acid polypeptides and are formed in human and other mammalian cells and tissues from the corresponding big endothelin (BETs) precursors through hydrolysis of a $Trp^{21}$-$Val^{22}$ or a $Trp^{21}$-$Ile^{22}$ bond by ECE to form the ETs. ETs have potent and sustained smooth muscle contractile actions, in particular ET-1 and ET-2 are the most potent and long-acting of known vasoconstrictor substances.

ETs are known to be associated with a wide variety of pathological states (Doherty A. M. J.Med.Chem 35/9 p1493–1508[1992]) and it has been postulated that there may exist the potential for therapy of such disease states by interference with ET receptors (Doherty A. M. ibid) or by inhibition of ECEs (JP 4-41430, WO 92/13545 and WO 92/12170).

A class of compounds has now been found which are effective ECE inhibitors. Such compounds are useful in treatment of myocardial infarction, angina pectoris, cerebral infarction (stroke), cerebral vasospasm, ischemic cardiac insufficiency, Raynaud's disease and other vasospastic diseases, atherosclerosis, essential hypertension, pulmonary hypertension, asthma, respiratory distress syndrome, acute renal failure, cyclosporin-induced renal failure, endotoxic shock, endotoxin-induced multiple organ failure, acute failure following organ trasplantation, Crohn's disease, ulcerative colitis, gastric ulcer, escleroderma and lupus erythematosus.

The present invention provides peptide compounds of formula (I) or a salt thereof,

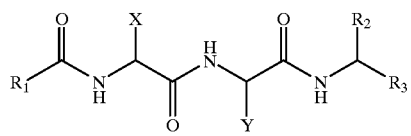

wherein:

$R_1$ is $C_{5-7}$ aryl; $C_{5-7}$ aryl $C_{1-7}$ alkyl; $C_{5-7}$ aryl $C_{1-4}$ alkoxy; $C_{5-7}$ aryloxy-$C_{1-4}$ alkyl; carboxy $C_{1-4}$ alkyl; $C_{1-4}$ alkoxycarbonyl $C_{1-4}$ alkyl; $C_{1-4}$ alkyl or di-phenyl $C_{1-4}$ alkyl, such aryl groups or aryl moieties of aryl-containing groups being optionally substituted with $C_{1-4}$ alkyl, halo, nitro, carboxyl or sulphonyl, or $R_1$ is a group of formula IIa, IIb or IIc:

IIa

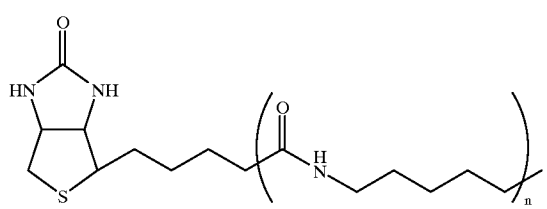

where n=0 or 1;

IIb

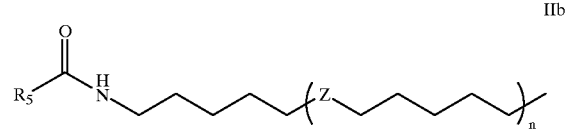

where n=0 or 1 and where Z is —CONH— or —$CH_2$— and $R_5$ is benzyloxy; 1,2,3,6tetrahydro-2,6-dioxo-4-pyrimidinyl; or 2,5dioxo-4-imidazolidinyl; or IIc

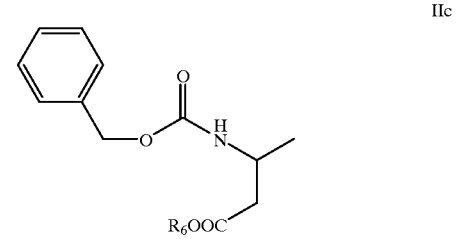

where $R_6$ is hydrogen or $C_{1-4}$ alkyl;

$R_2$ is indol-3-yl-methyl; $C_{5-7}$ aryl; or $C_{5-7}$ aryl $C_{1-4}$ alkyl, such aryl groups or aryl-moieties of aryl-containing groups being optionally substituted with hydroxy or halo; benzothienylmethyl; or $C_{1-4}$ alkyl;

$R_3$ is formyl; maleimidomethyl; methoxycarbonylvinyl; dimethoxymethyl; semicarbazonomethyl; $C_{1-4}$ alkyl; $R_4$ dithio; $R_4$ dithio-$C_{1-4}$ alkyl; $R_4$ dithioacetyl; $R_7$ $C_{1-4}$ alkylamido; $R_7$ $C_{1-4}$ alkylamidomethyl; —$COR_8$; —$CH(OH)R_9$; —$COCOR_{10}$; or —$COC\equiv CR_{11}$, in which $R_4$ is $C_{1-4}$ alkyl, $C_{5-7}$ aryl or $C_{1-4}$ alkyl $C_{5-7}$ aryl; $R_7$ is acetoxy, halo, maleimido or hydroxy; $R_8$ is

CHO; $C_{1-4}$ alkenyl, $C_{1-4}$ alkyhalo or $C_{1-4}$ alkylthio; $R_9$ is CHO, $C_{1-4}$ alkenyl or

such oxiranyl moiety being optionally substituted with $C_{1-4}$ alkyl or $C_{1-4}$ alkoxycarbonyl; $R_{10}$ is $C_{1-4}$ alkoxy; $C_{5-7}$ aryloxy; $C_{1-4}$ alkyl, hydrogen; hydroxy or methoxycarbonyl; and $R_{11}$ is hydrogen or $Si(CH_3)$; such aryl groups or aryl moieties of aryl-containing groups being optionally substituted with nitro or carboxy;

X is benzyl optionally substituted with $C_{1-4}$ alkoxy or halo; $C_{1-4}$ alkyl; indol-3-yl-methyl; naphthylmethyl; benzyloxybenzyl or cyclo $C_{1-6}$ alkylmethyl; and Y is benzyl optionally substituted with $C_{1-4}$ alkyl or $C_{1-4}$ alkoxy; indol-3-yl-methyl; naphthylmethyl; benzyloxybenzyl or $C_{1-4}$ alkyl.

Preferably $R_1$ is $C_{5-7}$ aryl $C_{1-4}$ alkoxy; $C_{5-7}$ aryl $C_{1-4}$ alkyl; $C_{5-7}$ aryloxy $C_{1-4}$ alkyl or is a group of Formula IIa or IIb where n=0 or 1 and where Z is —CONH— or —$CH_2$ and $R_5$ is benzyloxy; 1,2,3,6tetrahydro-2,6-dioxo-4-pyrimidinyl or 2,5,dioxo-4-imidazolidinyl, or is a group of Formula IIc where $R_6$ is hydrogen or $C_{1-4}$ alkyl.

Preferably R₂ is indol-3yl-methyl; phenyl or benzyl optionally substituted with halo or hydroxy.

Preferably R₃ is formyl; semicarbazonomethyl; —COR₈; R₇ C₁₋₄ alkylamido or R₇ C₁₋₄ alkylamidomethyl; in which R₈ is

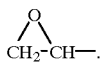

CHO; C₁₋₄ alkenyl, C₁₋₄ alkylhalo or C₁₋₄ alkylthio and R₇ is acetoxy, halo, maleimido, or hydroxy.

Preferably X is benzyl optionally substituted with halo; indol-3-yl-methyl; naphthyl-methyl; C₁₋₄ alkyl; or benzyloxybenzyl.

Preferably Y is naphthylmethyl; indol-3-yl-methyl, benzyloxybenzyl; C₁₋₄ alkyl; benzyloxyC₁₋₄ alkyl.

More preferably R₁ is benzyloxy; [5-(hexahydro-2-oxo-1H-thieno(3,4-d]imidazol-4-yl)valeramido]pentyl; 6-[6-[(1, 2,3,6-tetrahydro-2,6-dioxo-4-pyrimidinyl)formamido] hexanamido]pentyl; 6-[6-(benzyloxy)formamido] hexanamido]pentyl; 12-[(benzyloxy)acetamido]undecanyl; 5-phenylbutyl; phenoxyethyl; 5-(hexahydro-2-oxo-( 1H-thieno(3,4-d)imidazol-4-yl)butyl; 3-pyridylmethoxy; benzyl; 2-phenylethyl, 3-phenylethyl; N-[(benzyloxy) carbonyl)]-4-O-tert-butyl-L-aspart-1-yl; N-[(benzyloxy) carbonyl)]-L-aspart-1-yl; 6-[6-[2-(2,5-dioxo-4-imidazolidinyl) acetamido]hexanamido]pentyl; 3-pyridylmethoxy; 6-benzyloxycarbonylaminopentyl.

More preferably, R₂ is indol-3-yl methyl, chlorobenzyl; bromobenzyl; phenyl; benzyl, 4-hydroxybenzyl.

More preferably, R₃ is formyl; 2-oxiranylcarbonyl; semicarbazonomethyl; glyoxyloyl; acryloyl; chloroacetyl; 2-chloroacetyl; 2-acetoxyacetamido; (2-chloro-acetamido) methyl; (2-maleimidoacetamido)-methyl; 3-(malemidoacetamido)-methyl; 1-maleimidomethyl; propynoyl; (3-maleimidopropionamido)methyl.

More preferably, X is indol-3-yl-methyl; bromobenzyl; 1-naphthylmethyl; iodobenzyl; benzyloxybenzyl; [S]-1-methylpropyl; 2-napthylmethyl; benzyl; methyl; 4-chlorobenzyl; 2-methylpropyl; 1-methylethyl.

More preferably, Y is indol-3-yl-methyl; 1'-naphthylmethyl; 2-napthylmethyl; benzyloxybenzyl; 4-ethoxybenzyl; [S]-methylpropyl and, 1-methylethyl.

Particularly preferred compounds of the present invention are those wherein R₁ is 5-(hexahydro-2-oxo-1Hthieno[3,4-d]imidazol-4-yl)butyl or benzyloxy; R₂ is indol-3-yl-methyl or phenyl and R₃ is formyl or oxiranylcarbonyl; X is bromobenzyl, iodobenzyl or indol-3-yl-methyl, and Y is 2-napthylmethyl or indol-3-yl-methyl.

Most preferred embodiments of the present invention include compounds selected from the group comprising:

N-[[5-(hexahydro-2-oxo-1H-thieno[3,4-d]imidazol-4-yl) pentanoyl]-1-p-bromophenylalanyl-L-1-naphthylalanyl-L-N-[1-formyl]2-(1H-indol-3-yl)ethyl]amide; or N-[[5-(hexahydro-2-oxo-1H-thieno[3,4-d]imidazol-4-yl) pentanoyl]-L-tryptophanyl-L-tryptophanyl-L-N-[1-formyl] 2-(1H-indol-3-yl)ethyl]amide; or N-[(benzyloxy)carbonyl-L-p-bromophenylalanyl-L-1-naphthylalanyl-L-N-[1-[2-oxiranylcarbonyl]]2-phenylethyl] amide, N-[(benzyloxy)carbonyl-L-p-bromophenylalanyl-L-1-naphthylalanyl-1-L-formyl-1-(1H-indol-3-yl-methyl)-methyl]amide, N-[(benzyloxy)carbonyl-L-p-bromophenylalanyl-L-2-naphthylalanyl-1-L-formyl-1-(1H-indol-3-yl-methyl)-methyl]amide, N-[(benzyloxy)carbonyl-L-tryptophanyl-L-1-naphthylalanyl-1-L-formyl-1-(1H-indol-3-yl-methyl)-methyl]amide; or a salt thereof.

N-[(benzyloxy)carbonyl-L-p-iodophenylalanyl-L-1-naphthylalanyl-1-L-formyl-1-(1H-indol-3-yl-methyl)-methyl]amide, N-[[5-(hexahydro-2-oxo-1H-thieno[3,4-d]imidazol-4-yl) pentanoyl]-L-p-bromophenylalanyl-L-1-naphthylalanyl-L-N-[1-formyl]2-(1H-indol-3-yl)ethyl]amide, N-[[5-(hexahydro-2-oxo-1H-thieno[3,4-d]imidazol-4-yl) pentanoyl]-L-tryptothanyl-L-tryptophan-L-N-[1-formyl]2-(1H-indol-3-yl)ethyl]amide, N-(benzyloxy)carbonyl-L-p-bromophenylalanyl-L-1-naphthylalanyl-L-N-[1-[2-oxiranylcarbonyl]2-phenylethyl] amide, and N-[(benzyloxy)carbonyl-L-p-bromophenylalanyl-L-1-naphthylalanyl-1-L-formyl-1-(1H-indol-3-yl-methyl)-methyl]amide; or a salt thereof.

The present invention further comprises a compound of Formula (III) or a salt thereof;

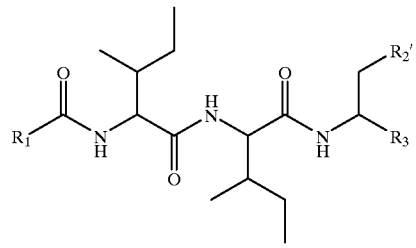

wherein

R₁ is selected from the group comprising C₅₋₇ aryl; C₅₋₇ aryl C₁₋₄ alkyl; carboxy C₁₋₄ alkyl; C₁₋₄ alkyl and C₅₋₇ aryl C₁₋₄ alkoxy; such aryl groups or aryl moieties of aryl-containing groups being optionally substituted with C₁₋₄ alkyl, halo, nitro, carboxyl or sulphonyl; wherein R₂ is methylR₂ and R₂ is selected from the group comprising indol-3-yl; phenyl; isobutyl and benzothienyl; and R₃ is selected from the group comprising formyl; glyoxyloyl; haloacetyl; C₁₋₄ alkoxalyl; C₅₋₇ aryloxalyl; R₄ dithio; R₄ dithio C₁₋₄ alkyl; dithioacetyl; ₁₋₄ alkyl; acryloyl and 2-oxiranylcarbonyl such oxiranyl being optionally substituted with a C₁₋₄ alkyl or C₁₋₄ alkoxycarbonyl and R₄ is selected from the group comprising C₁₋₄ alkyl, C₅₋₇ aryl and C₁₋₄ alkyl C₅₋₇ aryl; such aryl groups or aryl moieties of aryl-containing groups being optionally substituted with nitro or carboxyl.

Compounds of the present invention may exist as different optical isomers the nature of which will depend upon whether each modified amino acid residue is present in its S or R chiral form. The present invention includes within its scope each possible optical isomer substantially free ie associated with less than 5%, of any other optical isomer(s), and mixtures of one or more optical isomers in any proportions, including racemic mixtures.

Preferred compounds of the present invention include those wherein all chiral centres are present in their S chiral form.

Compounds of formula (I) wherein R₃ is formyl may be prepared by reduction of their respective N,O-dimethylhydroxamide precursors with lithiumaluminium hydride (Fehrenta, J. A., Castro, B., Synthesis 1983 p676–678). The N,O-dimethylhydroxamide precursors may be obtained by coupling of a protected dipeptide (eg N-Benzyloxycarbonyl(CBZ)-isoleucyl-isoleucyl-OH:

Bachem Bioscience Inc.) with the appropriate amino acid N,O-dimethylhydroxamide (Nahm S., Weinreb S., Tet. Lett. 22 3815–3818, [1981]). or its hydrochloride salt. The amino acid N,O-dimethylhydroxamides may be prepared from carbobenzyloxy protected amino acids (Bachem Biosciences) and N,O-dimethylhydroxylamine (Fluka) under standard peptide coupling conditions (Houben-Weyl, Methoden Der Organischen Chemie, 4, Aufl., Vol. 15/1 E. Muller Ed. [1974]) followed by hydrogenolytic deprotection (Houben-Weyl ibid).

The aminoacid N,O-dimethylhydroxamide hydrochloride salts may be prepared from t-butyloxy-carbonyl (BOC) protected amino acids (Bachem Bioscience) and N,O-dimethylhydroxylamine (Fluka) in the manner described above, followed by acidolytic deprotection with 4N HCl/dioxane (Pierce) (Burton, J., Topper, R., Ehrlich, R. in Peptides: Structure and Biological Functions, Gross, E. and Meienhofer, J., Eds., Pierce, Rockford, Ill., 605–608,[1979].

Alternatively, the N,O-dimethylhydroxamide precursors may be obtained by coupling a CBZ-protected amino acid to the hydrochloride salt of a dipeptide N,O-dimethylhydroxamide under standard peptide coupling conditions (Houben-Weyl, ibid.). The hydrochloride salt of the dipeptide N,O-dimethyl-hydroxamide may be obtained from acidolysis of the corresponding Boc-protected dipeptide N,O-dimethylhydroxamide using 4N HCl/dioxane in the manner previously described. The Boc-protected dipeptide N,O-dimethyl-hydroxamide may in turn be prepared by coupling a Boc-protected amino acid with the hydrochloride salt of an amino acid N,O-dimethylhydroxamide under standard peptide coupling procedures (Houben-Weyl, ibid.).

In another method, the N,O-dimethylhydroxamide precursors may be obtained by treatment of the hydrochloride salt of a tripeptide N,O-dimethyl-hydroxamide with benzyl chloroformate (Bergmann, M., Zervas, L., Ber. dtsch. Chem. Ges. (1932), 65, 1192). The hydrochloride salt may be obtained by acidolysis of the corresponding Boc-protected tripeptide N,O-dimethyl-hydroxamide using 4N HCl/dioxane as previously described. The Boc-protected tripeptide may be obtained by coupling a Boc-protected amino acid to the hydrochloride salt of a dipeptide N,O-dimethylhydroxamide under standard peptide coupling conditions (Houben-Weyl, ibid).

Additionally, the N,O-dimethylhydroxamide precursors may be synthesized by reacting a CBZ-protected amino acid with the free amine of a dipeptide N,O-dimethylhydroxamide under standard peptide coupling conditions (Houben-Weyl, ibid.). The dipeptide N,O-dimethylhydroxamide may be prepared by hydrogenolysis of a CBZ-protected dipeptide N,O-dimethylhydroxamide. The CBZ-protected dipeptide N,O-dimethylhydroxyamide may in turn be synthesized by reacting a CBZ-protected dipeptide with N,O-dimethylhydroxylamine.

Compounds of formula (I) wherein $R_3$ is acryloyl may be prepared from N,O-dimethylhydroxamide precursors by treatment with excess vinyl magnesium bromide (Lancaster Chemicals), (Nahm and Weinreb ibid). The synthesis of such N,O-dimethylhydroxamide precursors is discussed above.

Compounds of formula (I) wherein $R_3$ is 3-(trimethylsilyl)-2-propynoyl are prepared from the N,O-dimethylhydroxamide precursors by treatment with excess lithiated trimethylsilylacetylene (Aldrich Chemicals) (Nahm and Weinreb, ibid). The synthesis of the N,O-dimethylhydroxamide precursors is discussed above.

Compounds of formula (I) wherein $R_3$ is 2-alkynyl are prepared from compounds of formula (I) where $R_3$ is 3-(trimethylsilyl)-2-propynoyl described above, by treatment with methanolic sodiumbicarbonate.

Compounds of formula (I) wherein $R_3$ is (E)-2-methoxycarbonyl)vinyl are prepared from compounds of formula (I) by treatment with methoxycarbonylmethyltriphenylphosphorane (Aldrich Chemicals).

Compounds of formula (I) wherein $R_3$ is glyoxyloyl may be obtained from compounds of formula (I) wherein $R_3$ is acryloyl (described above) by ozonolysis, followed by reduction with dimethyl sulfide (Angelastro et al., J.Med.Chem. 33 13–16, 1990).

Compounds of formula (I) wherein $R_3$ is 2-oxiranylcarbonyl are prepared from compounds of formula (I) wherein $R_3$ is acryloyl (described above) by reduction to the allylic alcohol derivative (Luche, J. L., J.Am.Chem.Soc., 1978, 2227–2228), followed by oxidation with m-chloroperbenzoic acid (Cella, J. A., McGrath, J. P., Kelly, J. A., El Soukkary, O., Hilpert, L., J.Org.Chem, 1977, 42, 2077–2080) to the oxiranyl alcohol and further oxidation with dimethylsulfoxide/acetic anhydride (Mancuse, A. J., Swen, D., Synthesis, 1981, 165–185).

Compounds of formula (I) wherein $R_3$ is 1-hydroxyallyl are prepared by reduction of compounds of formula (I) where $R_3$ is acryloyl according to Luche, J. L. J.Am. Chem. Soc., 1978,2227–2228.

Compounds of formula (I) wherein $R_3$ is hydroxy(2-oxiranyl)methyl are prepared from compounds of formula (I) where $R_3$ is 1-hydroxyallyl by oxidation with m-chloroperbenzoic acid (Cella, J. A., McGrath, J. P., Kelly, J. A, El Soukkary, O., Hilpert, L., J.Org.Chem 1977, 42, 2077–2080).

Compounds of formula (I) wherein $R_3$ is formylhydroxymethyl are prepared from compounds of formula (I) where $R_3$ is 1-hydroxyallyl, by ozonolysis, followed by reduction with dimethylsulfide (Angelastro et al, J.Med.Chem. 1990, 33, 13–16).

Compounds of formula (I) wherein $R_3$ is haloacetyl may be obtained by coupling of N-protected dipeptide (eg CBZ-isoleucyl-isoleucyl-OH from Bachem Bioscience, Inc.) with the appropriate amino acid halomethylketone using a standard peptide coupling reaction. The halomethylketones may be prepared from commercially purchased amino acids (Bachem Biosciences, Inc.) using published procedures (Garcia-Lopez, M. T., Gonzalez-Muniz R., Harto, J. R. Tetrahedron, 1988, p 5131–5138) followed by deprotection with trifluoroacetic acid (Houben-Weyl ibid).

Compounds of formula (I) wherein $R_3$ is alkoxalyl may be obtained by ozonolysis of the 2-alkoxyvinyl ketone precursor followed by reduction with dimethylsulphide (Angelastro M. R., et al J.Med.Chem. 33 13–16, 1990). The precursor may be prepared from the appropriate N,O-dimethylhydroxamide precursor by addition of lithiated alkylvinylether (Angelastro et al ibid).

Compounds of formula (I) wherein $R_3$ is dimethoxymethyl are prepared from compounds of formula (I) where $R_3$ is formyl by treatment with trimethylorthoformate and pyridinium p-toluenesulfonate in methanol (Meskens et al, Synthesis 1981, 1501–1521).

Compounds of formula (I) wherein $R_3$ is pyruvoyl are prepared by hydrolysis of the 2-alkoxyvinyl ketone precursor (Angelastro M. R. el al J.MedChem. 1990, 33, 13–16). The precursor may be obtained from the appropriate N,O-dimethylhydroxamide precursor by addition of lithiated alkylvinylether (Angelastro et al, ibid).

Compounds of formula (I) wherein $R_3$ is semicarbazonomethyl are prepared from compounds of formula (I) where $R_3$ is formyl by treatment with semicarbazide and sodium acetate.

Compounds of formula (I) wherein $R_3$ is 2-(acetylthio) acetyl are prepared from compounds of formula (I) where $R_3$ is 2-chloroacetyl (see above) by treatment with thioacetic acid (Aldrich Chemicals) (Spaltenstein et al, J.Org.Chem., 1987 52, 3759–3766).

Compounds of formula (I) wherein $R_3$ is $R_4$-dithiomethyl may be prepared by treatment of the methylenethiol precursor with the appropriate mixed disulfide containing $R_4$-thiol and 5-nitropyridine-2-thiol. The mixed disulfides may be obtained by disulfide exchange reaction between commercially available 2,2'-dithiobis(5-nitropyridine) (Janssen Chemicals) and the desired thiol (Aldrich Chemicals) (Trans, J. P., Shen Z-Y, Int. J.Peptide Pro.Res., 1992, 39, 464–471 and Fournic-Zaluski, M-C., J.Med.Chem., 1992, 35, 2472–2481). Methylenethiol precursors may be prepared from commercially available (Bachem Biosciences) Boc-amino alcohols by treatment with methanesulfonyl chloride, followed by potassium thioacetate (Spaltenstein et al, ibid) and deprotection with trifluoroacetic acid and ammonium hydroxide (Houben-Weyl, ibid), followed by coupling to commercially available CBZ-protected dipeptides (Bachem Bioscience) (Houben-Weyl, ibid).

Compounds of formula (I) wherein $R_3$ is $R_4$dithioalkyl or $R_4$dithioacetyl alkyl may be prepared by treatment of the methylenethiol or thiomethylketone repectively precursor with the appropriate mixed disulphide containing 5 nitropyridine-2-thiol. The mixed disulphides may be obtained by a disulphide exchange reaction between commercially available 2,2'dithiobis(5-nitropyridine) (Janssen Chem) and the desired thiol (Trans, J. P., Shen Z-Y, Int. J. Peptide Protein Res., 1992 39 464–471 and Fournic-Zaluski M-C. et al. J. of Med. Chem. 1992 35 2473–2481). The thiols are either commercially available, or are themselves the thiomethylketones or methylenethiols described immediately hereafter.

These thiomethylketone precursors may be obtained from chloromethylketones such as compounds of formula (I) wherein $R_3$ is haloacetyl (synthesis ibid) by treating with thioacetic acid (Aldrich Chemicals) (Spaltenstein, A. et al J.Org.Chem. 1987, 52 3759–3766) followed by deprotection with ammonium hydroxide (Houben-Weyl ibid). Methylenethiols may be prepared from commercially available (Bachem Bioscience, Inc.) Boc-aminoalcohols by treatment with methanesulfonyl chloride, followed by potassium thioacetate (Spaltenstein et al ibid) and deprotection with trifluoroacetic acid and ammonium hydroxide (Houben-Weyl ibid).

Compounds of formula (I) wherein $R_3$ is glycolylamidomethyl, 2-chloroacetamidomethyl, 2-maleimidoacetamidomethyl, 3-maleimidoacetamidomethyl and [[[3-(ethoxycarbonyl)2-oxiranyl]carbonyl]amino]methyl are prepared by acylation of the methyleneamino precursor with appropriate commercially available (Aldrich and TCI Chemicals) acid precursor (Houben-Weyl, ibid). The methyleneamino precursors may be obtained by reduction of the corresponding azido compounds with triphenylphosphine in aqueous tetrahydrofuran. The azido compounds in turn are prepared from commercially available Boc-aminoalcohols (Bachem Biosciences) by mesylation, followed by displacement with lithium azide (Spaltenstein et al, ibid), deprotection with trifluoroacetic acid and coupling with the appropriate commercially available dipeptide (Bachem Biosciences) (Houben-Weyl, ibid).

Compounds of formula (I) wherein $R_3$ is 2-acetoxyacetamido are prepared from the corresponding free amino compounds by acylation with commercially available acetoxyacetylchloride (Aldrich Chemicals). The amino precursors are obtained by deprotecting the corresponding Boc-geminal diamide with trifluoroacetic acid (Houben-Weyl), ibid). The germinal diamide compounds are obtained by coupling the appropriate dipeptide with the mono protected geminal diamine, which in turn is obtained from the N-Cbz-N'-Boc protected diamino precursor by treatment with hydrogen over palladium on carbon. The protected diamine precursor is obtained from commercially available Boc-amino acids via a Hoffman degradation reaction.

Some $R_3$ groups may exist as different optical isomers and the present invention includes within its scope each possible optical isomer ie. S or R chiral form.

Compounds of formula (I) wherein $R_1$ is benzyloxy or 3-pyridinylmethoxy are prepared from the N,O-dimethylhydroxamide precursor described earlier by hydrogenation over palladium (Houben-Weyl, ibid), followed by acylation with the commercially available chloroformate (Aldrich Chemicals) and reduction with lithium aluminum hydride (Nahm and Weinreb, ibid).

Compounds of formula (I) wherein $R_3$ is maleimidomethyl are prepared from the aminomethyl precursor described above by treatment with maleic anhydride, followed by ring-closure with cyanuric fluoride.

Compounds of formula (I) wherein $R_3$ is methoxycarbonylglyoxyloyl are prepared from the corresponding tripeptides according to the procedure of Li (Li, Z. et al., J.Med.Chem. 1993, 36, 3472–3480).

Compounds odf formula (I) wherein $R_3$ is oxalyl are prepared from their ethylesters (described above) by alkaline hydrolysis under standard conditions.

All other compounds of the formula (I) where $R_1$ is not benzyloxy may be prepared from the compound of formula (I) where $R_1$ is H and $R_3$ is dimethoxymethyl by coupling of the corresponding acids according to known procedures (Houben-Weyl, ibid). The required precursor of formula (I) is obtained by deprotection of the previously described compound of formula (I) where $R_3$ is dimethoxymethyl and $R_1$ is benzyloxycarbonyl by hydrogenation over palladium (Houben-Weyl, ibid). The required acids are either commercially available or are prepared from commercially available materials (Aldrich Chemicals) by utilising standard peptide coupling procedures (Houben-Weyl, ibid).

All $R_1$ (N-protecting) groups may be introduced by treating the free amino group of the corresponding precursor with either the acid anhydride or acid chloride derivative (Aldrich, Janssen Chemicals) of the respective protecting group in pyridine (Houben-Weyl ibid). The precursors are obtained from corresponding carbobenzoxy derivatives by hydrogenation or treatment wit hydrobromic acid in acetic acid (Houben-Weyl ibid).

A further aspect of the present invention comprises a compound of formula (IV) or a salt thereof:

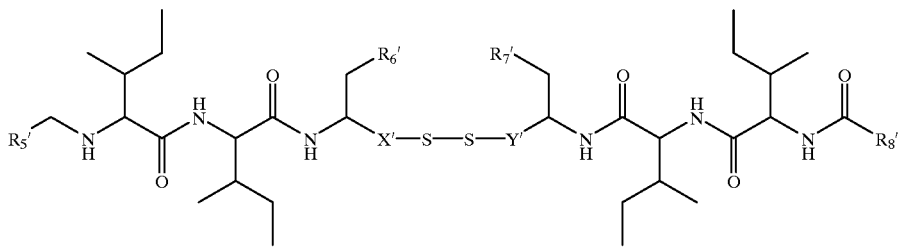

wherein $R_5'$ and $R_8'$ may be defined in the same way as $R_1$ above, $R_6'$ and $R_7'$ may be defined in the same way as $R_2$ above and X' and Y' may each be carbonylmethylene or methylene.

Preferred compounds of formula (IV) according to the invention include those wherein X' and Y' are defined as above, $R_6'$ and $R_7'$ are indol-3-yl and $R_5'$ and $R_8'$ are each independently selected from the group comprising phenyl, benzyl, 2-phenylethyl, benzyloxy, 2-carboxyethyl and methyl and are most preferably benzyloxy.

It will be appreciated that all of the compounds of general formula (II) are modified hexapeptides comprising four isoleucine residues and two further amino acid residues, the natures of which are defined by $R_6'$ and $R_7'$ respectively.

Compounds of formula (IV) be prepared by reacting a mixed disulphide with the appropriate methylenethiol (when X' is methylene) or thiomethylketone when X' is carbonylmethylene), containing the desired $R_5'$ and $R_8'$ group. When $R_5'$=$R_8'$ the compound is obtained by exposing the corresponding thiol compound (Step 3, Example 57) to air. The mixed disulfide may be obtained by a disulfide exchange reaction between commercially available 2,2'dithiobis(5-nitropyridine) (ibid) and the desired thiol (containing the appropriate $R_7$ and $R_8$ groups). The appropriate methylenethiol or thiomethylketone may be obtained as described for compounds of formula (I).

Salts of compounds of formula (I), (III) and (IV) are included within the scope of the invention and include base-addition salts when for example a carboxy group is present and acid-addition salts when for example a heterocyclic aryl group containing a nitrogen is present. Preferred salts of compounds of formula (I), (III) and (IV) are pharmaceutically acceptable salts.

All compounds referred to in the description of processes for synthesis of compounds of the present invention should be taken to be in the appropriate chiral form for synthesising the desired enantiomer or mixture of enantiomers.

According to the present invention there is also provided a method for the treatment of a cardiovascular disorder and more particularly myocardial infarction, angina pectoris, cerebral infarction (stroke), cerebral vasospasm, ischemic cardiac insufficiency, Raynaud's disease and other vasospastic diseases, atherosclerosis, essential hypertension, pulmonary hypertension, asthma, respiratory distress syndrome, acute renal failure, cyclosporin-induced renal failure, endotoxin shock, endotoxin-induced multiple organ failure, acute failure following organ transplantation, Crohn's disease, ulcerative colitis, gastric ulcer, esclero-derma and lupus erythematosus, which comprises the administration to a patient requiring such treatment of a therapeutically effective amount of one or more of a compound or salt or formulation according to the present invention.

According to a further feature of the invention there is provided the use of a compound or salt or formulation as defined herein in the manufacture of a medicament for use in therapy of one or more of the cardiovascular disorders described above.

According to a further feature of the invention there is provided a pharmaceutical composition which comprises a compound of the present invention, or a pharmaceutically acceptable salt thereof, in association with a pharmaceutically acceptable diluent or carrier.

The composition may be in a form suitable for oral use, for example a tablet, capsule, aqueous or oily solution, suspension or emulsion; for nasal use, for example, a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients. However, in the case of a composition for oral administration, it may be convenient for the composition to include a coating to protect the peptide active ingredient from the actions of enzymes in the stomach.

A preferred composition of the invention is, for example, one suitable for oral administration in unit dosage, for example a tablet or capsule which contains from 2.5 to 500 mg, and preferably 2 to 200 mg, of peptide in each unit dose to deliver a dose of from 0.05 mg/kg to 50 mg/kg, or one suitable for parenteral administration which contains from 0.5 to 100 mg of peptide per ml, and preferably 1 to 10 mg of peptide per ml of solution, to deliver a dose of from 1 mg/kg to 10 mg/kg bodyweight.

A parenteral composition is preferably a solution in isotonic saline or isotonic dextrose buffered if necessary to a pH of 5 to 9. Alternatively, the parenteral composition may be one designed for slow release in which case the amount of polypeptide per unit dose is in general greater than that required when a conventional injectable formulation is used. A preferred slow release formulation is, for example, a continuous release formulation, for example a formulation of the type described in U.S. Pat. No. 4,767,628 and U.S. Pat. No. 5,004,602 which are incorporated herein in their entirety. A preferred slow release parenteral formulation contains from 10 to 100 mg of polypeptide per unit dose. Another preferred slow release formulation is a microencapsulated polypeptide using a biodegradable biocompatible copolymer.

EXAMPLE 1

Synthesis of N-α-CBZ-S-Amino Acid-N-Methyl-O-Methyl-Hydroxyamides

A solution of N-α-CBZ-amino acid-OH (10 mmol), N,O-dimethylhydroxylamine hydrochloride (11 mmol), N-methylmorpholine (12 mmol), and 1-hydroxybenzotriazole (12 mmol) in dimethylformamide (50 mL) was treated with 1-ethyl-3-(3-dimethylaminopropyl)carbodiimide hydrochloride (11 mmol), and the resulting solution was stirred for 12 h at 25° C. DMF was removed in vacuo at 40° C. The residue was dissolved in ethyl acetate. The organics were washed successively with 5% NaHCO$_3$, 5% citric acid, and saturated NaCI. The organic phase was then dried with anhyd MgSO$_4$ and was concentrated in vacuo. Compounds were purified by flash chromatography or recrystallization.

EXAMPLE 2

Synthesis of N-α-Boc-S-Amino Acid-N-Methyl-O-Methyl-Hydroxamides

A solution of Boc-amino acid-OH (3 mmol), N,O-dimethylhydroxylamine hydrochloride (3.1 mmol), 1-hydroxybenzotriazole (3 mmol), and triethyl-amine (3.1 mmol) in DMF (5 mL) was cooled to 0° C. After 10 min, 1-ethyl-3-(3-dimethylaminopropyl)carbodiimide hydrochloride (3 mmol) was added, and the reaction proceeded for 18 h with gradual warming to 25° C. DMF was removed in vacuo, and the residue was partitioned between 10% Na$_2$CO$_3$ and EtOAc. The aq layer was extracted twice more with EtOAc. The EtOAc fractions were combined and washed with 10% Na$_2$CO$_3$, 1N HCl, and saturated NaCl. After drying over anhyd MgSO$_4$, the EtOAc layer was filtered and concentrated in vacuo. Compounds were purified by flash chromatography or recrystallisation.

EXAMPLE 3

Synthesis of HCl-S-Amino Acid-N-Methyl-O-Methyl-Hydroxamides

Boc-S-amino acid-N-methyl-O-methyl-hydroxamides (*2.5 mmol) were treated with 4N HCl/dioxane (10 mL) for 40 min. Dioxane was removed in vacuo. The residue was triturated twice with ethyl ether. Ether was removed and the products were dried in vacuo in the presence of NaOH(s).

EXAMPLE 4

Synthesis of N-α-Boc-S-Amino-Acid-S-Amino Acid-N-Methyl-O-Methyl-Hydroxamides BOC-amino acid-OH (10 mmol) and HCl-S-aminoacid-N-methyl-O-methyl-hydroxamide (11 mmol) were dissolved in DMF (10 mL). The stirring solution was then cooled to 0° C. After 5 min, diisopropylethylamine (11 mmol), 1-hydroxybenzotriazole (10 mmol), and 1-ethyl-3-(3-dimethylaminopropyl)carbodiimide hydrochloride (10 mmol) were added to the flask. The reaction proceeded for 18 h with gradual warming to room temperature. DMF was removed in vacuo and the residue was partitioned between 10% Na$_2$CO$_3$ and EtOAc. The aq. layer was extracted twice more with EtOAc. The EtOAc fractions were combined and washed with 10% Na$_2$CO$_3$, 1N HCl, and saturated NaCl. After drying over anhyd MgSO4, the EtOAc layer was filtered and concentrated in vacuo. The products were purified by flash chromatography or recrystallisation.

EXAMPLE 5

Synthesis of HCl-S-Amino-Acid-S-Amino Acid-N-Methyl-O-Methyl-Hydroxamides

Synthesis was carried out in the manner described for HCl-S-amino acid-N-Methyl-O-Methyl-hydroxamides using N-α-Boc-S-amino-acid-S-aminoacid-Methyl-O-Methyl-hydroxamides as the starting material.

EXAMPLE 6

Synthesis of N-α-Boc-S-Amino-Acid-S-Amino Acid-S-Amino Acid-N-Methyl-O-Methyl-Hydroxamides Synthesis was performed in the manner described for N-α-Boc-S-amino acid-S-amino acid-N-methyl-O-methyl-hydroxamides using a Boc-S-amino acid and HCl-S-amino-acid-S-amino acid-N-methyl-O-methyl-hydroxamides.

EXAMPLE 7

Synthesis of HCl-S-Amino-Acid-S-Amino Acid-S-Amino Acid-N-Methyl-O-Methyl-Hydroxamides Synthesis was carried out in the manner described for HCl-S-amino acid-N-methyl-O-methyl-hydroxamides using N-α-Boc-S-amino-acid-S-amino acid-S-amino acid-N-methyl--methyl-hydroxamides as the starting material

EXAMPLE 8

Synthesis of N-α-CBZ-S-Amino Acid-S-Amino Acid-N-Methyl-O-Methyl-Hydroxamides Synthesis was carried out in the manner described for N-α-CBZ-S-amino acid-N-methyl-O-methyl-hydroxamides using N-α-CBZ-S-amino acid-S-amino acid-OH in place of N-α-CBZ-S-amino acid-OH.

EXAMPLE 9

Synthesis of N-α-CBZ-S-Amino Acid-S-Amino Acid-S-Amino Acid-N-Methyl-O-Methyl-Hydroxamides To a solution of N-α-CBZ-S-amino acid-N-methyl-O-methyl-hydroxamide (5 mmol) in methanol (100 mL) was added 10% Pd/C (50 mg). The mixture was stirred for 6 h under an H$_2$ atmosphere using a balloon. After filtration and concentration in vacuo, the white residue was dissolved in DMF (50 mL). CBZ-amino acid-amino acid-OH (5 mmol. Bachem. Switz.), 1-hydroxybenzotriazole (5 mmol), and 1-ethyl-3-(3-dimethylamino-propyl)carbodiimide hydrochloride (5 mmol) were added. The solution was stirred for 12 h. DMF was removed in vacuo at 40° C. The residue was dissolved in ethyl acetate and was washed with 5% NaHCO$_3$, 5% citric acid, and saturated NaCl. Organics were dried over anhyd MgSO$_4$, filtered, and concentrated in vacuo. A white solid (2,4 g) was obtained. Compounds were purified by flash chromatography or were recrystallised.

EXAMPLE 10

CBZ-amino acid-amino acid-OH (1.32 mmol) and HCl-S-amino acid-N-methyl-O-methyl-hydroxamide (1.4 mmol) were dissolved in DMF (5 mL). The stirring solution was then cooled to 0° C. After 5 min, diisopropylethylamine (1.4 mmol), 1-hydroxybenzotriazole (1.32 mmol), and 1-ethyl-3-(3-dimethyl-aminopropyl)carbodiimide hydrochloride (1.32 mmol) were added to the flask. The reaction proceeded for 18 h with gradual warming to room temperature. DMF was removed in vacuo, and the residue was partitioned between 10% Na$_2$CO$_3$ and EtOAc. The aq layer was extracted twice more with EtOAc. The EtOAc fractions were combined and washed with 10% Na$_2$CO$_3$, 1N HCl, and saturated NaCl. After drying over anhyd MgSO$_4$, the EtOAc layer was filtered and concentrated in vacuo. The products were purified by flash chromatography or recrystallisation.

EXAMPLE 11

CBZ-amino acid-OH (0.4 mmol), HCl-S-amino acid-S-amino acid-methyl-O-methyl-hydroxamide (0.47 mmol), 1-hydroxybenzotriazole (0.4 mmol), and triethylamine (0.47 mmol) were dissolved in DMF (5 mL), and the mixture was cooled to 0° C. After 10 min, 1-ethyl-3-(3-dimethylamino-propyl)carbodiimide (0.4 mmol) was added. The reaction proceeded for 18 h with gradual warming to 25° C. The reaction was worked up in the manner described in Example 10.

EXAMPLE 12

HCl-S-amino acid-S-amino acid-S-amino acid-N-methyl-O-methyl-hydroxamide (0.66 mmol) was suspended in a mixture of chloroform (25 mL) and 3N NaOH (12.7 mL) at 0° C. To the vigorously stirring solution was added benzyl chloroformate (1.96 mmol) dropwise. The reaction proceeded for 18 h with gradual warming to 25° C. The reaction mixture was then diluted with DCM (150 mL) and H$_2$O (50 mL). The organic layer was washed with saturated NaCl, dried over MgSO$_4$, filtered, and concentrated in vacuo to afford the product as an oil.

EXAMPLE 13

To a solution of N-α-CBZ-S-amino acid-S-amino acid-N-methyl-O-methyl hydroxamide (5 mmol) in methanol (150 mL) was added 5% Pd/C (200 mg). The mixture was stirred for 18 h under an H$_2$ atmosphere using a balloon. After filtration and concentration in vacuo, the residue was dissolved in DMF (10 mL). CBZ-amino acid-OH (8.5 mmol,), 1-hydroxybenzotriazole (8.5 mmol), and 1-ethyl-3-(3-dimethylamino-propyl)carbodiimide hydrochloride (8.5 mmol) were added. The solution was stirred for 24 h. DMF was removed in vacuo at 40° C. The residue was dissolved in ethyl acetate and was washed with 1N NaOH, 1N HCl, and saturated NaCl. Organics were dried over anhyd MgSO$_4$, filtered, and concentrated in vacuo. A white solid (2.4 g) was obtained. Compounds were purified by flash chromatography or were recrystallised.

EXAMPLE 14

Synthesis of N-α-CBZ-S-Amino Acid-S-Amino Acid-S-Amino Acid Aldehydes

THF (10 mL) and 1M lithium aluminum hydride (0.4 mmol) were cooled to −50° C. with stirring. Next, a solution of N-α-CBZ-S-amino acid-S-amino acid-S-amino acid-μ-methyl-O-methyl-hydroxamide (0.4 mmol) in THF (5 mL) was added dropwise. The reaction temperature then climbed to 0° C., and this temperature was maintained for 4 h. During this time, lithium aluminum hydride was added periodically until the reaction was complete by TLC analysis. The reaction mixture was again cooled to −50° C., and the reaction was quenched with 5% citric acid. The mixture was filtered on celite, and the filtrate was combined with EtOAc. The filtrate was then washed with 10% Na$_2$CO$_3$ and saturated NaCl. The organics were dried over MgSO$_4$, filtered, and concentrated in vacuo. Compounds were purified by flash chromatography or recrystallisation.

EXAMPLE 15

N-Benzyloxycarbonyl-S-isoleucyl-S-isoleucine 1-S-formyl-2-(1H-indol-3-yl]ethylamide silica gel (10% methanol/methylene chloride)
$^1$H NMR (DMSO) δ: 0.63–0.93 (12H), 0.98–1.8 (4H), 2.62–3.07 (2H), 3.84–4.51 (3H), 5.06 (2H), 6.17–6.21 (1H), 6.31–6.36 (1H), 6.93–7.83 (10H), 8.48–8.52 (1H), 9.47 (1H), 10.63–10.84 (1H)
LRMS (EI, m/e): 549 (M$^+$+1)
Anal. (1H$_2$O): C: 65.96, H: 7.60, N: 10.10

EXAMPLE 16

N-Benzyloxycarbonyl-S-isoleucyl-S-isoleucine 1-S-formyl-2-phenyl-ethylamide silica gel (10% methanol/methylene chloride)
$^1$H NMR (DMSO) δ: 0.77 (12H), 1.03 (2H), 1.39 (2H), 1.64 (2H), 2.7–3.1 (2H), 3.90 (1H), 4.22 (1H), 4.36 (1H), 5.02 (2H), 7.1–7.4 (11H), 7.75 (1H), 8.49 (1H), 9.42 (1H)
LRMS (EI, m/e): 511 (M+1)
Anal. C: 66.21, H: 7.59, N: 8.05

EXAMPLE 17

N-Benzyloxycarbonyl-S-isoleucyl-S-isoleucine 1-S-formyl-3-methyl-butylamide silica gel (10% methanol/methylene chloride)
$^1$H NMR (DMSO) δ: 0.72–0.9 (18H), 1.0–1.2 (1H), 1.25–1.75 (8H), 3.75–4.23 (3H), 5.03 (2H), 7.35 (5H), 9.37 (1H)
LRMS (EI, m/e): 476 (M$^+$+1)
Anal. (½H$_2$O): C: 64.49, H: 8.79, N: 8.60

EXAMPLE 18

N-Benzyloxycarbonyl-S-isoleucyl-S-isoleucine 1-S-formyl-2-(benzo-thien-3-yl)ethylamide silica gel (10% methanol/methylene chloride)
$^1$H NMR (DMSO) δ: 0.68–0.87 (12), 1.0–1.2 (2H), 1.3–1.8 (4H), 3.0–3.15 (2H), 3.88–4.0 (1H), 4.2–4.28 (1H), 4.49–4.62 (1H), 5.0–5.05 (2H), 7.28–7.48 (10H), 7.79–7.89 (1H), 7.92–8.03 (1H), 9.54 (1H)
LRMS (EI, m/e): 566 (M$^+$+1)
Anal. (½H$_2$O): C: 64.32, H: 7.18, N: 7.26

EXAMPLE 19

N-Benzyloxycarbonyl-S-p-bromophenylalnyl-S-(O-benzyl)tyrosyl-1-S-formyl-1-(1H-indol-3-yl-methyl)-methylamide 1H NMR (δ, DMSO-d$_6$): 2.6–3.2 (6H), 4.2–4.6 (3H), 4.8–5.1 (4H), 6.9–7.6 (24H), 8.2 (1H), 8.6 (1H), 9.4 (1H), 10.9 (1H)

EXAMPLE 20

N-Benzyloxycarbonyl-S-phenylalanyl-S-isoleucyl-1-S-formyl-1-(S)-1-methylpropylmethylamide 1H NMR (δ, CDCl$_3$): 0.8–1.1 (12H), 1.2–1.6 (4H), 1.9 (1H), 2.1 (1H), 3.1 (2H), 4.3 (1H), 4.4–4.6 (2H), 5.1 (2H), 5.2 (1H), 6.4 (2H), 7.2 (10H), 9.6 (1H)
LRMS (FAB): 510.4 (MH$^+$)

EXAMPLE 21

N-Bezyloxycarbonyl-S-alanyl-S-phenylalanyl-1-S-formyl-1-(2-S-butyl)-methylamide

1H NMR (δ, CDCl₃): 0.9 (6H), 1.3 (5H), 2.0 (1H), 3.1 (2H), 4.2 (1H), 4.4 (1H), 4.7 (1H), 5.1 (3H), 6.4 (1H), 6.6 (1H), 7.2–7.4 (10H), 9.5 (1H)

LRMS (FAB): 468.2 (MH⁺)

EXAMPLE 22

N-Benzyloxycarbonyl-S-isoleucyl-S-isoleucyl-1-S-formyl-1-(S)-1-methylpropyl)-methylamide 1H NMR (δ, CDCl₃): 0.8–1.3 (21H), 1.3–1.6 (3H), 1.7–2.1 (3H), 4.2 (1H), 4.4 (1H), 4.6 (1H), 5.1 (2H), 5.7–6.0 (1H), 7.0–7.2 (1H), 7.3 (6H), 9.6 (1H)

LRMS (FAB): 476.2 (MH⁺)

EXAMPLE 23

N-Benzyloxycarbonyl-S-isoleucyl-S-phenylalanyl-1-S-formyl-1-(S)-1-methylpropylbutyl-methylamide 1H NMR (δ, CDCl₃): 0.8–1.0 (12H), 1.0–1.4 (4H), 1.8–2.0 (2H), 3.1 (2H), 4.0 (1H), 4.4 (1H), 4.7 (1H), 5.1 (2H), 5.2 (1H), 6.5 (2H), 7.2–7.4 (10H), 9.5 (1H)

LRMS (FAB) 510.3 (MH⁺)

EXAMPLE 24

N-Benzyloxycarbonyl-S-valyl-S-isoleucyl-1-S-formyl-1-(1H-indo-3-yl-methyl-methylamide 1H NMR (δ, DMSO-d₆): 0.6–1.0 (12H), 1.0–1.5 (2H), 1.7 (1H), 2.0 (1H), 3.0–3.3 (2H), 3.9 (1H), 4.3 (1H), 4.5 (1H), 5.0 (2H), 7.0–7.4 (10H), 7.5 (1H), 7.8 (1H), 8.5 (1H), 9.5 (1H), 10.9 (1H)

LRMS (FAB): 535.5 (MH+)

EXAMPLE 25

N-Benzyloxycarbonyl-S-phenylalanyl-S-isoleucyl-1-S-formyl-1-(1H-indol-3-yl-methyl)-methylamide 1H NMR (δ, DMSO-d₆): 0.6–1.0 (6H), 1.0–1.8 (3H), 2.6–3.2 (4H), 4.2–4.5 (3H), 5.0 (2H), 7.0–7.6 (16H), 7.9 (1H), 8.5 (1H), 9.5 (1H), 10.9 (1H)

LRMS (FAB): 583.6 (MH⁺)

EXAMPLE 26

N-Benzyloxycarbonyl-S-alanyl-S-phenylalanyl-1-S-formyl-1-(1H-indol-3-yl-methyl)-methylamide 1H NMR (δ, DMSO-d₆): 1.1 (3H), 2.6–3.3 (4H), 4.1 (1H), 4.4 (1H), 4.6 (1H), 5.0 (2H), 7.0–7.6 (16H), 8.0 (1H) 8.5 (1H), 9.4 (1H), 10.9 (1H)

LRMS (FAB): 541.2 (MH⁺)

EXAMPLE 27

N-Benzyloxycarbonyl-S-isoleucyl-S-phenylalanyl-1-S-formyl-1-(1H-indol-3-yl-methyl)-methylamide 1H NMR (δ, DMSO-d₆): 0.7 (6H), 1.0 (1H), 1.3 (1H), 1.6 (1H), 2.7–3.3 (4H), 3.9 (1H), 4.4 (1H), 4.7 (1H), 5.0 (2H), 7.0–7.4 (15H), 7.5 (1H), 8.1 (1H), 8.5 (1H), 9.5 (1H), 10.9 (1H)

LRMS (FAB): 583.3 (MH⁺)

EXAMPLE 28

N-Benzyloxycarbonyl-S-leucyl-S-isoleucyl-1-S-formyl-1-(1H-indol-3-yl-methyl-methylamide 1H NMR (δ, DMSO-d₆): 0.8 (12H), 1.1 (1H), 1.4 (3H), 1.7 (2H), 2.9–3.3 (2H), 4.1 (1H), 4.3 (1H), 4.4 (1H), 5.0 (2H), 7.0–7.6 (11H), 7.7 (1H), 8.5 (1H), 9.5 (1H), 10.9 (1H)

LRMS (FAB): 549.5 (MH⁺)

EXAMPLE 29

N-Benzyloxycarbonyl-S-isoleucyl-S-valyl-1-S-formyl-1-(1H-indol-3-yl-methyl)-methylamide 1H NMR (δ, DMSO-d₆): 0.6–1.0 (12H), 1.1 (1H), 1.4 (1H), 1.7 (1H), 2.0 (1H), 3.0–3.3 (2H), 4.0 (1H), 4.3 (1H), 4.5 (1H), 5.0 (2H), 7.0–7.4 (10H), 7.5 (1H), 7.8 (1H), 8.5 (1H), 9.5 (1H), 10.9 (1H)

LRMS (FAB): 535.4 (MH⁺)

EXAMPLE 30

N-Benzyloxycarbonyl-S-isoleucyl-S-tryptophanyl-1-S-formyl-1-(1H-indol-3-yl-methyl)-methylamide 1H NMR (δ DMSO-d₆): 0.6–1.1 (8H), 1.6 (1H), 2.8–3.2 (4H), 3.9 (1H), 4.3 (1H), 4.6 (1H), 5.0 (2H), 6.9–7.6 (16H), 8.0 (1H), 8.5 (1H), 9.3 (1H), 10.8 (2H)

LRMS (FAB): 622.5 (MH⁺)

EXAMPLE 31

N-Benzyloxycarbonyl-S-tryptophanyl-S-tryptophanyl-1-S-formyl-1-(1H-indol-3-yl-methyl)-methylamide 1H NMR (δ DMSO-d₆): 2.8–3.3 (6H), 4.3 (2H), 4.7 (1H), 5.0 (2H), 6.9–7.7 (21H), 8.2 (1H), 8.5 (1H), 9.3 (1H), 10.8 (3H)

LRMS (FAB): 695.7 (MH⁺)

EXAMPLE 32

N-Benzyloxycarbonyl-S-phenylalanyl-S-phenylalanyl-1-S-formyl-1-(1H-indol-3-yl-methyl)-methylamide 1H NMR (δ, DMSO-d₆): 2.6–3.3 (6H), 4.3 (2H), 4.7 (1H), 5.0 (2H), 7.0–7.6 (21H), 8.2 (1H), 8.6 (1H), 9.4 (1H), 10.9 (1H)

LRMS (FAB): 617.3 (MH⁺)

EXAMPLE 33

N-Benzyloxycarbonyl-S-isoleucyl-S-isoleucyl-1-S-formyl-1-(4-hydroxy-benzyl)-methylamide 1H NMR (δ, DMSO-d₆): 0.8–1.0 (14H), 1.2–1.4 (2H), 1.5–1.8 (2H), 2.6 (1H), 3.0 (1H), 3.9 (1H), 4.2 (2H), 5.0 (2H), 6.6 (2H), 6.9 (2H), 7.3 (6H), 7.7 (1H), 8.4 (1H), 9.2 (1H), 9.4 (1H)

LRMS (FAB): 526.4 (MH⁺)

Anal.C: 65.21, H: 7.57, N: 7.76

EXAMPLE 34

N-Benzyloxycarbonyl-S-tryptophanyl-S-1'naphthylalanyl-1-S-formyl-1-(1H-indol-3-yl-methyl)-methylamide 1H NMR (δ, DMSO-d₆): 2.8–3.6 (6H), 4.2–4.5 (2H), 4.7–5.1 (3H), 6.9–8.0 (22H), 8.2 (1H), 8.3 (1H), 8.5 (1H), 9.4 (1H), 10.8 (1H), 10.9 (1H)

LRMS (FAB): 706.3 (MH⁺)

EXAMPLE 35

N-Benzyloxycarbonyl-S-tryptophanyl-S-2'naphthylalanyl-1-S-formyl-1-(1H-indol-3-yl-methyl)-methylamide 1H NMR (δ, DMSO-$d_6$): 2.7–3.5 (6H), 4.2 (1H), 4.4 (1H), 4.7 (1H), 4.1 (2H), 6.9–7.9 (23H), 8.2 (1H), 8.6 (1H), 9.4 (1H), 10.7 (1H), 10.9 (1H)

LRMS (Ion Spray): 765.3 (MH$^+$)

EXAMPLE 36

N-Benzyloxycarbonyl-S-tryptophanyl-S-(O-benzyl)tyrosyl-1-S-formyl-1-(1H-indol-3-yl-methyl)-methylamide 1H NMR (δ, DMSO-$d_6$): 2.7–3.3 (6H), 4.3 (2H), 4.6 (1H), 5.0 (4H), 6.6–7.7 (25H), 8.0 (1H), 8.6 (1H), 9.4 (1H), 10.8 (1H), 10.9 (1H)

LRMS (Ion Spray): 779.4 (M+NH$_4^{30}$)

EXAMPLE 37

N-Benzyloxycarbonyl-S-p-bromophenylalanyl-S-1'naphthylalanyl-1-S-formyl-1-(1H-indol-3-yl-methyl)-methylamide 1H NMR (δ DMSO-$d_6$): 2.5–3.5 (6H), 4.2–4.4 (2H), 4.7 (1H), 4.9 (2H), 6.9–7.6 (19H), 7.8 (1H), 7.9 (1H), 8.1 (1H), 8.4 (1H), 8.6 (1H), 9.4 (1H), 10.8 (1H)

LRMS (FAB): 745.2, 747.2 (MH$^+$

EXAMPLE 38

N-Benzyloxycarbonyl-S-p-bromophenylalanyl-S-2'naphthylalanyl-1-S-formyl-1-(1H-indol-3-yl-methyl)-methylamide 1H NMR (δ, DMSO-$d_6$): 2.6–3.3 (6H), 4.3 (1H), 4.4 (1H), 4.7 (1H), 4.9 (2H), 7.0–7.9 (22H), 8.3 (1H), 8.6 (1H), 9.5 (1H), 10.9 (1H)

LRMS (Ion Spray): 799.5 (M+Na+MeOH)

EXAMPLE 39

N-Benzyloxycarbonyl-S-1'naphthylalanyl-S-(O-benzyl)tyrosyl-1-S-formyl-1-(4-chlorophenylmethyl)-methyloamide 1H NMR (δ, DMSO-$d_6$): 2.7–3.2 (6H), 4.2–4.4 (2H), 4.9 (2H), 5.0 (1H), 5.1 (2H), 6.9–8.2 (27H), 8.6 (1H), 9.4 (1H)

LRMS (Ion Spray): 768.3 (MH$^+$)

EXAMPLE 40

N-Benzyloxycarbonyl-S-p-iodophenylalanyl-S-1'naphthylalanyl-1-S-formyl-1-(1H-indol-3-yl-methyl)-methylamide 1H NMR (δ, DMSO-$d_6$): 2.6–3.3 (6H), 4.3 (2H), 4.8 (1H), 5.0 (2H), 6.6–8.0 (21H), 8.2 (1H), 8.4 (1H), 8.6 (1H), 9.4 (1H), 10.8 (1H), 4.8 (1H)

LRMS (FAB): 793.2

EXAMPLE 41

N-Benzyloxycarbonyl-L-isoleucyl-L-isoleucine-L-N-[1-acryloyl-2-(1H-indol-3-yl)ethyl]amide A solution of 1.2 g (2 mMol) of Z-Ile-Ile-Trp-N-methyl-N-methoxyamide (see above), in 10 mL of tetrahydrofuran was cooled to −78° and treated with 22 mL (22 mMol) of vinylmagnesium bromide (1M in THF). The reaction mixture was allowed to warm to 25° and was stirred at that temperature for 24 h. The resulting mixture was poured into excess 1N hydrochloric acid and extracted with ethylacetate. Evaporation of the solvent followed by chromatography on silica gel (1:1 hexanes/ethyl acetate) and trituration with ether afforded the desired vinyl ketone as a white solid (0.4 g 1st crop, 0.3 g 2nd crop).

1H-NMR (CDCl$_3$): δ 0.79 (12H), 1.02 (2H), 1.28 (2H), 2.70 (2H), 3.02 (2H), 3.92 (1H), 4.22 (1H), 4.83 (1H), 5.01 (2H), 5.78 (1H), 6.19 (1H), 6.50 (1H), 6.96 (1H), 7.02 (1H), 7.08 (1H), 7.30 (7H), 7.5 (1H), 7.78 (1H), 8.41 (1H), 10.80 (1H).

LRMS: (FAB): 575 (M$^+$+1)

Anal.: C,H,N.

EXAMPLE 42

N-Benzyloxycarbonyl-L-isoleucyl-L-isoleucine-L-N-[1-acryloyl-2-(phenyl)ethyl]amide This compound was obtained using the procedure employed in Example 41, starting with the corresponding Cbz-IleIlePhe amide precursor 1H-NMR (DMSO $d_6$) 0.78 (12H), 1.04 (2H), 1.38 (2H), 1.66 (2H), 2.80 (1H), 3.00 (1H), 3.92 (1H), 4.21 (1H), 4.79 (1H), 5.01 (2H), 5.80 (1H), 6.22 (1H), 6.56 (1H), 7.1–7.4 (11H), 7.7 (1H), 8.4 (1H)

LRMS (FAB): 536.5 (M+1)

Anal: C,H,N

EXAMPLE 43

N-Benzyloxycarbonyl-L-isoleucyl-L-isoleucine-L-N-[1-(1-hydroxyallyl)-2-(phenyl)ethyl]amide A suspension of 3.6 g (6.6 mMol) of the vinyl ketone obtained in Example 42 in 300 mL of methanol was treated with 3.6 g (10 mMol) of cerium-III-chloride heptahydrate and then cooled on an ice-bath. 0.5 g (13.5 mMol) of sodium borohydride was added scoopwise over 10 minutes and the resulting mixture was stirred for 1 h and then quenched with saturated aqueous ammonium chloride solution. Extraction with chloroform, drying over magnesium sulfate and removal of the solvent in vacuo, followed by trituration with ether afforded the desired allylic alcohol (3.2 g) as a white solid and as a mixture (approximately 1:1) of diastereomers.

1H-NMR (DMSO $d_6$): 0.83 (12H), 1.00 (2H), 1.38 (2H), 1.83 (2H), 2.60 (1H), 2.82 (2H), 3.85–4.15 (3H), 5.00 (3H), 5.20 (1H), 5.82 (2H), 7–7.4 (10H), 7.6 (1H), 7.7 (1H).

LRMS (FAB): 539 (M$^+$+1)

Anal: C,H,N

EXAMPLE 44

N-Benzyloxycarbonyl-L-isoleucyl-L-isoleucine-L-N-[1-[1-hydroxy(1-oxiranyl)methyl-2-(phenyl)ethyl]amide A solution of 0.5 g (0.93 mMol) of the allylic alcohol obtained in Example 43, in 300 mL of 1:1 chloroform-methanol was treated with 8 g of m-chloroperbenzoic acid at 25°. The resulting mixture was stirred for 8 h and extracted with 1N sodium hydroxide solution. Drying over magnesium sulfate and removal of the solvent in vacuo, followed by trituration with 10% tetrahydrofuran-ether, afforded the desired epoxide (0.4 g) as a mixture of four diastereomers.

1H-NMR (DMSO-d$_6$): 0.78 (12H), 1.05 (2H), 1.38 (2H), 1.70 (2H), 2.58 (2H), 2.72 (1H), 2.90 (2H), 3.08 (1H), 4.15 (2H), 5.05 (2H), 7.1–7.4 (10H), 7.6 (1H), 7.75 (1H)

LRMS (FAB): 555

Anal: C,H,N

EXAMPLE 45

N-Benzyloxycarbonyl-L-isoleucyl-L-isoleucine-L-N-[1-[2-oxiranylcarbonyl]-2-(phenyl)ethyl]amide A solution of 0.1 g (0.18 mMol) of the epoxide obtained in Example 44, in 5 mL of dimethylsulfoxide and 1 mL of acetic anhydride was stirred at 25° for 3 days. The resulting mixture was poured into water and centrifuged. The solids were collected and triturated with ether to afford the desired ketoepoxide as a white solid (0.05 g) as a mixture of two diastereomers (~1:1).

1H-NMR (DMSO d$_6$) 0.78 (12H), 1.03 (2H), 1.38 (2H), 1.65 (2H), 2.80 (2H), 2.95 (1H), 3.16 (1H), 3.66 (1H), 3.92 (1H), 4.20 (1H), 4.70 (1H), 5.02 (2H), 7.2–7.4 (10H), 7.7 (1H), 8.58 (1H)

LRMS (FAB): 553 (M+1)

Anal: C,H,N

EXAMPLE 46

N-Benzyloxycarbonyl-L-isoleucyl-L-isoleucine-L-N-[1-glyoxyloyl-2-(phenyl)ethyl]amide A solution of 1.0 g (1.8 mMol) of the vinylketone obtained in Example 42, in 400 mL of 4:1 Chloroform-methanol was cooled to −78° and treated with a stream of ozone until a blue color was observed. The resulting mixture was treated with 10 mL of dimethylsulfide and allowed to warm to 25°. The volatiles were evaporated in vacuo and the residue was triturated with 10% tetrahydrofuran-ether to give the desired ketoaldehyde (0.75 g) as a pale yellow solid).

1H-NMR (DMSO d$_6$) 0.75 (12H), 1.05 (2H), 1.38 (2H), 1.65 (2H), 2.85 (2H), 3.85 (1H), 4.18 (2H), 5.00 (3H), 7–7.4 (10H), 7.6 (1H), 8.7 (1H)

LRMS (FAB): 539 (M+1)

Anal: C,H,N

EXAMPLE 47

N-Benzyloxycarbonyl-L-isoleucyl-L-isoleucine-L-N-[1-formylhydroxymethyl-2-(phenylethyl]amide)

15 g of the allylic alcohol obtained in Example 43 was treated in an identical fashion to the procedure outlined in Example 46 to give the desired aldehyde (0.12 g) as a white solid and as a 1:1 mixture of diastereomers.

1H-NMR (DMSO d$_6$) 0.72 (12H), 1.02 (2H), 1.39 (2H), 1.63 (2H), 2.70 (1H), 2.82 (1H), 3.30 (1H), 3.95 (2H), 4.20 (2H), 5.00 (2H), 5.6 and 6.8 (1H), 7–7.4 (10H), 7.6 (1H), 7.8–8.1 (1H), 9.42 (1H)

LRMS(FAB): 541 (M+1)

Anal.: C,H,N

EXAMPLE 48

N-Benzyloxycarbonyl-L-isoleucyl-L-isoleucine-L-N-[1[3-[trimethylsilyl]-2-propynoyl]2-(1H-indol-3-yl)ethyl]amide A solution of 2.8 g (20 mMol) of trimethylsilylacetylene (Aldrich Chemicals) in 10 mL of tetrahydrofuran was cooled to −78° and treated with 13.3 mL of 1.5 n n-butyllithium. The resulting solution was stirred at −78° for 10 min and then treated with 1.2 g (2 mMol) of the N,O-domethylhydroxamide of Cbz-lIelle Trp described above. The mixture was stirred for 1 h and then allowed to warm to 25° over 2 h. Saturated aqueous amonium chloride was added and the volatiles were removed in vacuo. The residue was chromatographed on silica gel with 75% ethyl acetate-hexane to give the desired propargyl ketone as a beige solid (0.15 g).

1H-NMR (CDCl$_3$) 0.21 (9H), 0.81 (12H), 1.15 (2H), 1.40 (2H), 1.80 (2H), 3.40 (2H), 3.98 (1H), 4.28 (1H), 5.01 (1H), 5.05 (2H), 5.23 (1H), 6.38 (1H), 6.99 (1H), 7.18 (1H), 7.19 (1H), 7.38 (7H), 7.60 (1H), 8.22 (1H)

LRMS (FAB): 645 (M+1)

Anal: C,H,N

EXAMPLE 49

N-Benzyloxycarbonyl-L-isoleucyl-L-isoleucine-L-N-[1[2-propynoyl]2-(1H-indol-3-yl)ethyl]amide A solution of the silylated compound described in Example 48 (0.05 g, 0.08 mMol) in 1 mL of methanol was treated with 0.1 mL of saturated aqueous sodium bicarbonate. The resulting mixture was evaporated and chromatographed on silica gel with 35% ethylacetatehexanes to give the desired propargyl ketone as a pale beige solid (0.03 g).

1H-NMR (CD$_3$OD 0.6–0.8 (12H), 1.10 (2H), 1.40 (2H), 1.6–1.8 (2H), 3.17 (1H), 3.40 (1H), 3.95 (1H), 4.00 (1H), 4.21 (1H), 4.80 (1H), 5.03 (2H), 7.0–7.4 (10H)

LRMS (FAB): 573 (M+1)

Anal.: C,H,N

EXAMPLE 50

N-Benzyloxycarbonyl-L-isoleucyl-L-isoleucine-L-N-[1-dimethoxymethyl-2-(1H-indol-3-yl)ethyl]amide A solution of 0.25 g (0.47 mMol) of the aldehyde compound obtained in Example 15, in 3 mL of methanol and 1 mL of trimethylorthoformate was treated with 0.05 g of pyridinium p-toluenesulfonate. The resulting mixture was stirred at 25° for 12 h and the volatiles were removed in vacuo. The residue was partitioned between ethyl acetate and 1N hydrochloric acid and the organic layer was washed with saturated aqueous sodium bicarbonate. Drying over magnesium sulfate, removal of the volatiles in vacuo and trituration with ether afforded the desired acetal as a white solid (0.2 g)

1H-NMR (DMSO d$_6$) 0.78 (12H), 1.05 (2H), 1.38 (2H), 1.70 (2H), 2.77 (1H), 2.92 (1H), 3.28 (3H), 3.31 (3H, 3.95 (1H), 4.20 (3H), 5.01 (2H), 6.95 (1H), 7.02 (2H), 7.25–7.4 (7H), 7.48 (1H), 7.7 (1H), 7.8 (1H), 10.72 (1H)

LRMS (FAB): 596 (M+1)

Anal.: C,H,N

EXAMPLE 51

N-Benzyloxycarbonyl-L-isoleucyl-L-isoleucine-L-N-[(E)-2-(methoxycarbonyl)vinyl]2-(1H-indol-3-yl)ethyl]amide A solution of 5.0 g (27 mMol) of trimethylphosphonoacetate (Aldrich Chemicals) in 50 mL of tetrahydrofuran was treated with 0.3 g (12.5 mMol) of sodium hydride. The resulting thick slurry was stirred at 25° for 0.5 h and then treated with a solution of 0.5 g (1 mMol) of Cbz-llelleTrp aldehyde described in Example 15, in 10 mL if tetrahydrofuran. The resulting mixture was stirred at 25° for 1 h and diluted with ethylacetate. Extraction with saturated ammonium chloride solution, drying over magnesium sulfate and removal of the solvent in vacuo, followed by a plug-filtration on silica get (35% ethylacetate-hexanes) afforded the desired ester as a 5:1 mixture of trans:cis isomers and as a white solid (0.4 g).

1H-NMR (DMSO $d_6$) 0.75 (12H), 1.05 (2H), 1.38 (2H), 1.70 (2H), 2.94 (2H) 3.95 (0.8H,trans), 4.00 (0.2H,cis), 4.15 (0.2H,cis), 4.18 (0.8H,trans), 4.78 (1H), 5.02 (2HO, 5.79 (0.2H,cis), 5.82 (0.8H,trans), 6.11 (0.2H,cis), 6.87 (0.8H, tans), 6.92 (1H), 7.08 (1H), 7.14 (1H), 7.3 (7H), 7.51 (0.8H), 7.57 (0.2H)

LRMS (FAB): 606 (M+1)

Anal. C,H,N

EXAMPLE 52

N-Benzyloxycarbonyl-L-isoleucyl-L-isoleucine-L-N-[1pyruvoyl]2-(phenyl)ethyl]amide Step 1: A solution of 15 mL (~150 mMol) of ethylvinylether (Aldrich Chemicals) in 50 mL of tetrahydrofuran was cooled to −78° and treated with 75 mL (130 mMol) of 1.7M tert-butyllithium in hexanes. The resulting mixture was warmed to −40° and cooled back to −78° and then treated with a solution of 8.0 g (15 mMol) of Cbz-llellePhe-N,O-dimethylhydroxamide (described above) in 10 mL of tetrahydrofuran. The reaction was quenched with saturated aqueous ammonium chloride and extracted with ethyl acetate. Drying over magnesium sulfate and removal of the volatiles in vacuo, followed by recrystallisation from tetrahydrofuran afforded the enolether intermediate (4.6 g) as a white solid.

Step 2: A solution of 0.75 g (1.3 mMol) of the enolether of Step 1 in 50 mL of tetrahydrofuran was treated with 5 mL of concentrated hydrochloric acid. The resulting mixture was stirred for 4 h at 25° and then extracted with ethyl acetate. The organic layer was washed with saturated aqueous sodium bicarbonate, dried over magnesium sulfate and concentrated in vacuo. Trituration with 10% tetrahydrofuran-ether afforded the desired ketocarbonyl compound as a white solid (0.55 g).

1H-NMR (DMSO-$d_6$): enolether Step 1: 0.78 (12H), 1.05 (2H), 1.38 (2H), 1.65 (2H), 2.72 (1H), 2.98 (1H), 3.77 (2H), 3.85 (1H), 4.22 (1H), 4.62 (1H), 5.02 (2H), 5.17 (1H), 5.19 (1H), 7.2–7.4(11H), 7.62 (1H), 8.2 (1H), Step 2: 0.78 (12H), 1.05 (2H), 1.38 (2H), 1.68 (2H), 2.18 (3H), 2.80 (1H), 3.08 (1H), 3.93 (1H), 4.20 (1H), 4.86 (1H), 5.02 (2H), 7.15–7.4 (11H), 7.75 (1H), 8.78 (1H), LRMS (FAB): enolether Step 1: 581 (M+1) Step 2: 553 (M+1)

Anal.: Step 1: C,H,N Step 2: C,H,N.

EXAMPLE 53

N-Benzloxycarbonyl-L-isoleucyl-L-isoleucine-L-N-[1-ethoxalyl]2-(phenyl)ethyl]amide A solution of 2.0 g (3.6 mMol) of the enolether intermediate described in step 1 of Example 52, in 130 mL of chloroform-methanol (4:1) was cooled to −78° and a stream of ozone was passed through the mixture for 5 minutes. 10 mL of dimethylsulfide were added and the mixture was allowed to warm to 25°. The volatiles were evaporated in vacuo and the residue was recrystallised from 10% tetrahydrofuran-ether to afford the desired ester as a white solid (1.25 g).

1H-NMR )DMSO-$d_6$): 0.75 (12H), 1.10 (2H), 1.18 (3H), 1.38 (2H), 1.62 (2H), 2.85 (1H), 3.13 (1 H), 3.92 (1H), 4.18 (2H), 4.25 (1H), 5.00 (1H), 5.02 (2H), 7.15–7.4 (1H), 7.72 (1H), 8.65 (1H),

LRMS (FAB): 583 (M+1)

Anal.: C,H,N

EXAMPLE 54

N-Benzyloxycarbonyl-L-isoleucyl-L-isoleucine-L-N-[1{2-chloroacetyl]2-(1H-indol-3-yl)ethyl]amide Step 1 Boc-Trp-chloromethylketone: A solution of 45 g (150 mMol) of Boc-Tryptophan (Bachem Bioscience) in 500 mL of tetrahydrofuran was treated with 24.3 mL of triethylamine and cooled to 0°, 16.7 mL (175 mMol) of ethylchloroformate was added dropwise, the resulting mixture was stirred for 2 h at 0° and then filtered. The filtrate was cooled back to 0° and treated with ~250 mMol of diazomethane in ether, stirred for 2 h and then treated with 36 mL of 4M hydrogen chloride in dioxane. After stirring for 1 h, the volatiles were removed in vacuo and the residue was partitioned between ether and saturated aqueous sodium bicarbonate. Drying over magnesium sulfate, removal of the solvent in vacuo and chromatography on silica gel (40% ethyl acetate-hexanes) afforded the desired chloromethylketone (10 g) as a white solid.

Step 2: 1.7 g (5 mMol) of the chloromethylketone from step 1 were treated with 50 mL of 4M hydrogen chloride in dioxane. The mixture was stirred for 0.5 h and the volatiles were removed in vacuo. In a separate flask, a solution of 1.25 g (3.3 mMol) of Cbz-llelle (Bachem Biosciences) in 10 mL of tetrahydrofuran and 0.487 mL of triethylamine was cooled to 0° and treated with 0.333 mL (3.5 mMol) of ethylchloroformate. The mixture was stirred for 1 h at 0°, filtered and treated with a solution of the residue of flask 1 in 10 ml of tetrahydrofuran. 0.3 mL of triethylamine were added and the resulting mixture was stirred for 12 h at 25°. Dilution with ethylacetate and extraction with 1N hydrochloric acid and saturated aqueous sodium bicarbonate, followed by drying over magnesium sulfate, removal of the solvent in vacuo and chromatography on silica gel (ethylacetate) afforded the desired compound as a beige solid (0.4 g).

1H-NMR Step 1 (CDCl$_3$): 1.38 (9H), 3.21 (2H), 4.02 (2H), 4.77 (1H), 5.18 (1H), 7.00 (1H), 7.18 (1H), 7.20 (1H), 7.38 (1H), 7.61 (1H), 8.18 (1H). Step 2 (DMSO-$d_6$) 0.78 (12H), 1.05 (2H), 1.38 (2H), 1.70 (2H), 3.00 (1H), 3.18 (1H), 3.95 (1H), 4.20 (1H), 4.22 (1H), 4.65 (1H), 5.00 (2H), 6.97 (1H), 7.00 (1H), 7.14 (1H), 7.23 (6H), 7.44 (1H), 7.63 (1H), 8.38 (1H), 10.65 (1H)

LRMS (FAB Step 1: 338 (M+1) Step 2: 599 (M+1)

Anal: Step 1: C,H,N,CI Step 2: C,H,N,CI

EXAMPLE 55

N-Benzyloxycarbonyl-L-isoleucyl-L_isoleucine-L-N-[1[2-(acetylthio)acetyl]2-phenyl)ethyl]amide A solution of 0.5 g (0.9 mMol) of Cbz-llellePhe-chloromethylketone (prepared in an identical fashion as outlined for Cbz-llelleTrp-chloromethylketone in Example 54) in 2 mL of tetrahydrofuran and 3 mL of methanol was purged with nitrogen and treated with 1.0 g (8.9 mMol) of potassiumthioacetate. The mixture was stirred for 12 h and diluted with ethyl acetate. Extraction with saturated aqueous sodium bicarbonate, followed by drying over magnesium sulfate, removal of the solvent in vacuo and chromatography on silica gel (1% ethanol/dichloromethane) afforded the desired compound as a white solid (0.1 g).

1H-NMR (DMSO-$d_6$): 0.80 (12H), 1.05 (2H), 1.40 (2H), 1.65 (2H), 2.38 (3H), 2.80 (1H), 3.18 (1H), 3.92 (1H), 3.98 (2H), 4.20 (1H), 4.68 (1H), 5.02 (2H), 7.1–7.4 (11H), 7.80 (1H), 8.50 (1H)

LRMS (FAB): 598.7 (M+1)

Anal.: C,H,N,S

EXAMPLE 56

N-Benzyloxycarbonyl-L-isoleucyl-L-isoleucine-L-N-[1[semicarbazonomethyl]2-(1H-indol-3-yl)ethyl] amide A solution of the aldehyde compound obtained in Example 15 (5 g) in 100 mL of ethanol was treated with a solution of 2 g of semicarbazide hydrochloride and 1.5 g of sodium acetate in 50 mL of water. The resulting mixture was refluxed for 2 h, cooled and diluted with 300 mL of water. Extraction with ethylacetate and evaporation of the volatiles in vacuo, followed by recrystallisation from aqueous ethanol afforded the semicarbazone (2 g) as a white solid.

LRMS (FAB): 607 (M+1)

Anal.: C,H,N

EXAMPLE 57

N-(benzyloxy)carbonyl-L-isoleucyl-L-isoleucine-L-N[1-[[(5-nitro-2-pyridyl)dithio]methyl]-2-(1H-indol-3-yl)ethyl]amide Step 1: A solution of 20 g (69 mMol) of Boc-tryptophanol (Bachem Biosciences) and 11.2 mL of triethylamine in 400 mL of dichloromethane was treated with 8.8 g (77 mMol) of methanesulfonyl chloride at 25° over 0.5 h. The resulting mixture was extracted with 1N aqueous hydrochloric acid and saturated aqueous sodium bicarbonate dried over magnesium sulfate and concentrated in vacuo. Recrystallisation from dichloromethane-hexanes afforded the desired mesylate (22.1 g) as a white solid.

Step 2: A solution of 9.0 g (24 mMol), of the mesylate from Step 1 and 3.5 g (31 mMol) of potassium thioacetate in 100 mL of acetonitrile was stirred for 12 h at 25° and then heated to 50° for 0.5 h. the reaction was diluted with ether and extracted with water. Drying over magnesium sulfate and removal of the solvent in vacuo, followed by chromatography on silica gel (20% ethylacetate/hexane) gave the desired thioacetate (5.7 g) as a beige solid. Step 3: A solution of 1.5 g (6.6 mMol) of the thioacetate from Step 2 in 50 mL of 2M ammonia in methanol was stirred at 25° for 12 h. the volatiles were removed in vacuo and the residue was dissolved in 50 mL of 4M hydrogen chloride in 1,4-dioxane. The resulting solution was stirred at 25° for 2 h and then concentrated in vacuo to give a brown foam, which was redissolved in 25 mL of dimethylformamide and treated with 3.4 g (9 mMol) of Cbz-isoleucylisoleucine (Bachem Biosciences), 1.3 g (9 mMol) of hydroxybenzotriazole. 1.7 g (9 mMol) of EDCI and 1.0 g (9 mMol) of triethylamine. The resulting mixture was stirred at 25° for 12 h and then concentrated in vacuo. The residue was partitioned between ethylacetate and 1N aqueous hydrochloric acid, the organic layer was washed with saturated aqueous sodium bicarbonate, dried over magnesium sulfate and concentrated in vacuo. Chromatography on silica gel (15% tertbutyl-methylether-dichloromethane) afforded the desired thiol (0.55 g) as a beige foam and the corresponding disulfide (0.3 g) as a pale yellow solid.

Step 4: A solution of 0.25 g (0.4 mMol) of the thiol obtained in Step 3 and 0.39 g (1.25 mMol) of 5,5'dinitro-2,2'-dithiobispryidine (Aldrich) in 5 mL of dimethylformamide was treated with 0.2 g of 4-dimethylaminopyridine and stirred at 25° for 5 days. The volatiles were removed in vacuo and the residue was chromatographed on silica gel (50% ethylacetate-hexane) to give the desired disulfide (0.05 g) as a yellow solid

1H-NMR

Step 1: (CDCl$_3$) 1.42 (12H), 3.98 (3H), 3.05 (2H), 4.20 (3H), 4.80 (1H), 7.1–7.3 (4H), 7.4 (1H), 7.58 (1H), 8.12 (1H)

Step 2: (CDCl$_3$) 1.42 (12H), 2.37 (3H), 2.98 (2H), 3.08 (2H), 4.10 (1H), 4.73 (1H), 7–7.4 (4H), 7.65 (1H), 8.27 (1H)

Step 3: (DMSO-$d_6$) 0.78 (12H), 1.07 (2H), 1.40 (2H), 1.70 (2H), 2.19 (1H), 2.58 (1H), 2.80 (2H), 3.02 (1H), 3.9–4.2 (3H), 4.99 (2H), 6.9–8 (14H), 10.80 (1H), Step 4: (CD$_3$OD) 0.85 (12H), 1.18 (2H), 1.55 (2H), 1.82 (2H), 2.88 (2H), 3.02 (2H), 3.99 (1H), 4.22 (1H), 4.50 (1H), 5.07 (2H), 6.92 (1H), 7.00 (2H), 7.2–7.4 (7H), 7.55 (1H), 7.72 (1H, 8.25 (1H), 9.00 (1H)

LRMS Step 1: 369, Step 2: 349, Step 3: 568 Step 4: 722

Anal.: Step 1: C,H,N,S Step 2: C,H,N,S Step 3: C,H,N,S Step 4: C,H,N,S

EXAMPLE 58

N--(3,3-diphenylpropionyl)-L-isoleucyl-L-isoleucine-L-N-[1-formyl]2-(1H-indol-3-yl)ethyl] amide Step 1: A solution of 1.9 g (3.2 mMol) of the compound of formula (I) where R3 is dimethoxymethyl (Example 50), in 200 mL of methanol was treated with 0.1 g 5% palladium on carbon and then stirred under an atmosphere of hydrogen gas for 0.5 h. The mixture was filtered through a layer of Celite and the volatiles were removed in vacuo to give the free amine as a white solid (1.2 g).

Step 2: A solution of 0.23 g (0.5 mMol) of the free amine from Step 1, 0.075 g (0.5 mMol) of 3,3-diphenylpropionic acid, 0.1 g (0.5 mMol) of EDCI, 0.08 g (0.5 mMol) of N-hydroxybenzotriazole in 2 mL of dimethylformamide was stirred at 25° for 12 h. The mixture was diluted with ethyl acetate and extracted with 1N aqueous hydrochlodic acid and saturated aqueous sodium bicarbonate. Drying over magnesium sulfate and removal of the volatiles in vacuo, followed by trituration with ether afforded the intermediate dimethylacetal as a white solid (0.2 g).

Step 3: A solution of 0.1 g (0.15 mMol) of the material obtained in Step 2 in 10 mL of tetrahydrofuran and 1 mL of 1N aqueous hydrochloric acid was heated to 70° for 2 h. The mixture was diluted with ethylacetate and extracted with saturated aqueous sodium bicarbonate. Drying over magnesium sulfate, removal of the solvent in vacuo and trituration with 10% ethylacetate/ether afforded the desired compound as a pale green solid) 0.06 g).

1H-NMR (DMSO-$d_6$): Step 1: 0.78 (12H), 1.02 (2H), 1.60 (2H), 2.77 (1H), 2.92 (2H), 3.21 (1H), 3.24 (6H), 4.20 (3H), 6.95–7.05 (3H), 7.35 (1H), 7.48 (1H), 7.95 (2H), 10.78 (1H)

Step 2: 0.57–0.82 (12H), 0.95 (1H), 1.15 (1H), 1.30 (1H), 1.58 (2H), 2.75 (2H), 2.90 (1H), 3.08 (1H), 3.27 (3H), 3.28 (3H), 4.0–4.2 (4H), 4.44 (1H), 6.9–7.35 (14H), 7.43 (1H), 7.64 (1H), 7.72 (1H), 7.95 (1H), 10.70 (1H)

Step 3: 0.5–0.9 (12H), 1.00 (1H), 1.05 (3H), 1.35 (1H), 1.60 (2H), 2.75 (1H), 2.98 (1H), 3.15 (2H), 4.10 (1H), 4.18 (1H), 4.42 (2H), 6.95–7.95 (14H), 7.48 (1H), 7.80 (1H), 7.85 (1H), 8.38 (1H), 9.42 (1H), 10.85 (1H)

LRMS (FAB): Step 1: 461.6 (M+1) Step 2: 670 (M+1) Step 3. 623.7 (M+1)

Anal.: Step 1: C,H,N Step 2: C,H,N Step 3: C,H,N

EXAMPLE 59

N-(3-Phenylpropionyl)-L-isoleucyl-L_isoleucine-L-N-[1-formyl]2-(1H-indol-3-yl)ethyl]amide Step 1: A solution of 0.23 g (0.5 mMol) of the product of Step 1 in Example 58 in 2 mL of dimethylformamide and 3 mL of pyridine was treated with 0.25 mL of 3-phenylpropionyl chloride (Aldrich Chemicals). The mixture was stirred at 25° for 4 h and quenched with 2 mL of water. After 3 h the volatiltes were removed in vacuo and the residue was partitioned between ethyl acetate and 1N aqueous hydrochloric acid, the organic layer was washed with saturated aqueous sodium bicarbonate, dried over magnesium sulphate and concentrated in vacuo. Trituration with ether afforded the desired dimethylacetal (0.2 g) as a white solid.

Step 2: 0.1 g of the product of Step 1 were treated in an analogous manner to Step 3 in Example 58, to afford the desired aldehyde (0.07 g) as a white solid.

1H-NMR (DMSO-$d_6$): Step 1: 0.75 (12H), 1.00 (2H), 1.38 (2H), 1.65 (2H), 2.41 (2H), 2.77 (3H), 2.90 (1H), 3.24 (3H), 3.25 (3H), 4.18 (4H), 6.98 (1H), 7–7.2 (7H), 7.28 (1H), 7.44 (1H), 7.73 (2H), 7.96 (1H), 10.72 (1H)

Step 2: 0.70 (12H), 0.98 (2H), 1.38 (2H), 1.63 (2H), 2.45 (2H), 2.65 (2H), 2.98 (1H), 3.18 (1H), 4.20 (2H), 4.40 (1H), 6.98 (1H), 7.02 (1H), 7.15–7.22 (6H), 7.25 (1H), 7.50 (1H), 7.78 (1H), 7.84 (1H), 8.40 (1H), 9.44(1H), 10.85 (1H)

LRMS (FAB): Step 1: 593.8 (M+1) Step 2: 547.7 (M+1)

Anal.: Step 1: C,H,N Step 2: C,H,N

EXAMPLE 60

N-acetyl-L-isoleucyl-L-isoleucine-L-N-[1-formyl]2-(1H-indol-3-yl)ethyl]amide

Step 1: A solution of 0.08 g (0.18 mMol) of the free amine obtained in Step 1 of Example 58 in 0.5 mL of pyridine was treated with 0.055 g (0.54 mMol) of acetic anhydride. The mixture was stirred at 0° for 3 h and the volatiles were removed in vacuo. The residue was partitioned between 1N aqueous hydrochloric acid and ethyl acetate and the organic layer was washed with saturated aqueous sodium bicarbonate. Drying over magnesium sulfate and removal of the volatiltes in vacuo afforded the desired acetal as a foam (0.14 g).

Step 2: The crude product from Step 1 was converted to the desired aldehyde (0.07 g off-white solid) in an analogous manner to the procedure use for Step 3 in example 58.

1H-NMR (CD$_3$OD): Step 1: 0.75–0.9 (12H), 1.00 (2H), 1.31 (2H), 1.45 (2H), 2.00 (3H), 2.88 (1H), 3.02 (1H), 3.38 (3H), 3.42 (3H), 4.00 (1H), 4.22 (1H), 6.95–7.1 (2H), 7.30 (1H), 7.55 (1H), 7.82 (1H)

Step 2: 0.7–1 (12H), 1.10 (2H), 1.50 (2H), 1.75 (2H), 1.98 (3H), 2.85 (1H), 3.08 (1H), 4.18 (3H), 4.50 (1H), 6.98–7.05 (5H), 7.25 (1H)

LRMS (FAB): Step 1: 503 (M+1) Step 2: 457 (M+1)

Anal.: Step 1: C,H,N Step 2: C,H,N

EXAMPLE 61

N-(3-Carboxypropionyl)-L-isoleucyl-L-isoleucine-L-N-[1-formyl]2-(1H-indol-3-yl)ethyl]amide A solution of 0.08 g (0.18 mMol) of the free amine obtained in Step 1 of Example 58 in 0.5 mL of pyridine was cooled to 0° and reacted with 0.027 g (0.27 mMol) of succinic anhydride. The mixture was stirred at 0° for 3 h and the volatiles were removed in vacuo. The residue was partitioned between ethyl acetate and 1N aqueous hydrochloric acid and the organic layer was washed with water. Drying over magnesium sulfate and removal of the solvent afforded the crude acetal (0.2 g) which was used in the next step without purification.

Step 2: The material from the first step was converted to the aldehyde in an analogous manner to Step 3 of Example 58 to give the desired product after chromatography on silica gel (6% methanol-dichloromethane) (beige foam).

1H-NMR (DMSO-$d_6$): Step 1: 0.82 (12H), 1.17 (2HO, 1.45 (2H), 1.80 (2H), 2.58 (4H), 2.84 (1H), 3.05 (1H), 3.37 (3H), 3.40 (3H, 4.20 (3H), 4.38 (1H), 7.03 (2H), 3.35 (1H), 7.55 (1H), 7.80 (1H)

Step 2: 0.65–0.85 (12H), 1.10 (2H), 1.40 (2H), 1.72 (2H), 2.40 (4H), 3.00 (1H), 3.20 (1H), 4.20 (2H), 4.42 (1H), 7.02 (2H), 7.18 (1H), 7.28 (1H), 7.59 (1H), 7.80 (1H), 7.95 (1H), 9.44 (1H), 10.88 (1H), LRMS (FAB): Step 1: 562 (M+1) Step 2: 515.5 (M+1)

Anal: Step 2: C,H,N

EXAMPLE 62

[[5-(hexahydro-2-oxo-1H-thieno[3,4-d]imidazol-4-yl]valeryl-L-isoleucyl-L-isoleucine-L-N-[1-dimethoxymethyl]2-(1H-indol-3-yl)ethyl]amide A solution of 0.358 g (0.8 mMol) of the free amine obtained in Step 1 of Example 58. 0.196 g (0.8 mMol) of biotin (Aldrich), 0.108 g (0.8 mMol) of hydroxybenzotriazole, 0.152 g (0.8 mMol), of EDCI and 0.08 g (0.8 mMol) of triethylamine in 6 mL of dimethylformamide was stirred for 15 h at 25°. The mixture was diluted with ethylacetate and water and the resulting precipitate was filtered to give the desired acetal as a white solid (0.47 g)

1H-NMR (DMSO-$d_6$): 0.78 (9H), 1.00–1.80 (13H), 2.18 (2H), 2.60 (2H), 2.7–3.1 ( ), 3.26 ( ), 3.27 (3H), 4.1–4.4 (4H), 6.4 (2H), 6.9–7.1 (2H), 7.38 (1H), 7.55 (1H), 7.75 (2H), 7.92 (1H), 10.75 (1H)

LRMS (FAB): 596 (M+1)

Anal: C,H,N,S

EXAMPLE 63

N-[[5-(hexahydro-2-oxo-1H-thieno[3,4-d]imidazol-4-yl]valeryl-L-isoleucyl-L-isoleucine-L-N-[1-formyl]2-(1H-indol-3-yl)ethyl]amide 0.4 g of the acetal obtained in Example 62 were converted to the aldehyde using a protocol analogous to that used in Step 3 of Example 58 to give the desired compound (0.05 g) as an off-white solid after chromatography on silica gel (5% methanol-dichloromethane).

1H-NMR (DMSO-$d_6$) 0.75 (12H), 1.00 (2H), 1.2–1.7 (8H), 2.10 (2H), 2.55 (1H), 2.6–3.1 (7H), 4.0–4.4 (4H), 6.4

(2H), 6.9–7.1 (2H), 7.35 (1H), 7.55 (2H), 7.7 (1H), 7.85 (1H), 9.44 (0.5H), 10.65 (1H)

LRMS: 642 (M+1)

Anal: C,H,N,S

EXAMPLE 64

N-[(benzyloxy)carbonyl]-4-O-tert-butyl-L-aspart-1-yl]-L-isoleucyl-L-isoleucine-L-N-[1-formyl]2-(1H-indol-3-yl)ethyl]amide Step 1: A solution of 0.23 g (0.5 mMol) of the free amine obtained from Step 3 in Example 58. 0.22 g (0.5 mMol) of Cbz-(t-bu)Asp-N-hydroxysuccinimide ester (Bachem Bioscienses) and 0.14 mL (1 mMol) of triethylamine in 5 mL of tetrahydrofuran and 5 mL of methanol was stirred at 25° for 72 h. The mixture was passed through a bed of DOWEX anionexchange resin (OH-form) and washed with methanol. The volatiles were removed in vacuo and the residue was redissolved in methanol. Water was added and the resulting precipitate was filtered and washed with water to give the desired acetal (0.4 g) as a white solid.

Step 2: A solution of 0.2 g (0.28 mMol) of the acetal from Step 1 in 10 mL of tetrahydrofuran and 1 mL of 1N aqueous hydrochloric acid was heated to 80° for 2 h. the mixture was diluted with ethyl acetate and extracted with saturated aqueous sodium bicarbonate. Drying over magnesium sulfate and removal of the solvent in vacuo afforded the desired aldehyde (0.08 g) as a white solid 1H-NMR (DMSO-$d_6$) : 0.75 (12H), 0.97 (2H), 1.35 (1H), 1.65 (2H), 2.40 (1H), 2.60 (1H), 2.95 (1H), 3.18 (1H), 4.18 (2H), 4.38 (2H), 5.00(2H), 6.8–8.0 (13H), 8.42 (1H), 9.42 (1H), 10.84 (1H)

EXAMPLE 65

N-[benzyloxy)carbonyl]-L-aspart-1-yl]-L-isoleucyl-L-isoleucine-L-N-[1-formyl]2-(1H-indol-3-yl)ethyl]amide Step 1: A solution of 0.1 g (0.13 mMol) of the acetal obtained in Step 1 of Example 64 in 10 mL of methanol was treated with 0.5 g of lithium hydroxide and stirred for 1 h at 25°. Ethyl acetate was added and the solution was extracted with 1N aqueous hydrochloric acid. Drying over magnesium sulfate and removal of the solvent in vacuo afforded the desired acid (0.1 g) as a beige solid.

Step 2: 0.08 g (0.1 mMol) of the acid of Step 1 were converted to the aldehyde following an analogous procedure to that used in Step 3 of Example 58 to give the desired compound (0.01 g) after chromatography on silica gel (5% methanol-dichloromethane). 1H-NMR (DMSO-$d_6$) 0.78 (12H), 1.05 (2H), 1.36 (2H), 1.8 (2H), 2.6 (2H), 2.8 (1H), 3.05 (1H), 4.04–4.4 (4H), 4.99 (2H), 6.8–7.6 (8H), 7.98 (1H), 9.41 (1H), 10.82 (1H),

LRMS: 665

EXAMPLE 66

N-[[[5-(hexahydro-2-oxo-1H-thieno[3,4-d]imidazol-4-yl)valeramido]hexanoyl]-L-isoleucyl-L-isoleucine-L-N-[1-dimethoxymethyl]2-(1H-indol-3-yl)ethyl]amide A solution of 0.07 g (0.16 mMol) of the free amine obtained in Step 1 of Example 58. 0.15 g (0.33 mMol) of biotinamidocaproate n-hydroxysuccinimide ester (Sigma Chemicals), and 0.1 mL of triethylamine in 5 mL of metha- nol and 5 mL of ethyl acetate was stirred at 25° for 12 h. The mixture was diluted with ethyl acetate and extracted with 1N aqueous hydrochloric acid and saturated aqueous sodium bicarbonate dried over magnesium sulfate and concentrated in vacuo to afford the desired acetal (0.1 g) as a beige solid.

1H-NMR (DMSO-$d_6$): 0.75 (12H), 0.9–1.8 (16H), 2.05 (4H), 2.5–3.1 (10H), 3.26 (6H), 4.1–4.4 (4H), 6.40 (2H), 6.9–7.1 (2H), 7.35 (1H), 7.52 (1H), 7.75 (2H), 7.92 (1H), 10.73 (1H)

LRMS (ESMS): 801 (M+1)

Anal: C,H,N,S

Step 2: 0.1 g of the acetal obtained in Step 1 was converted to the aldehyde utilizing a procedure similar to that used for Step 3 in Example 58 to give the desired compound as a light brown solid.

1H-NMR (DMSO-$d_6$): Step 1: 0.78 (12H), 1–1.8 (10H), 2.18 (2H), 2.79 (1H), 2.97 (3H), 3.37 (3H), 3.39 (3H), 4.02 (1H), 4.18 (3H), 5.02 (2H), 6.92–8.0 (14H), 10.84 (1H), Step 2: 0.78 (12H), 1.0–1.8 (10H), 2.17 (2H), 2.98 (3H), 3.20 (1H), 4.20 (2H), 4.42 (1H), 5.00 (2H), 6.95–8.0 (13H), 8.42 (1H), 9.46 (1H), 10.88 (1H)

LRMS: Step 1: 708 Step 2: 662.5

Anal.: Step 1: C,H,N.

EXAMPLE 67

N-[[[5-(hexahydro-2-oxo-1H-thieno[3,4-d]imidazol-4-yl)valeramido]hexanoyl]-L-isoleucyl-L-isoleucine-L-N-[1-formyl]2-(1H-indol-3-yl-ethyl]amide 0.2 g of the acetal obtained in Example 66 were converted to the aldehyde using an analogous procedure to that used for Step 3 in Example 58, to give the desired compound (0.098 g) as a white solid.

1H-NMR (DMSO-$d_6$) 0.75 (12H), 0.9–1.8 (16H), 2.10 (4H), 2.58 (1H), 2.80 (1H), 2.9–3.25 (8H), 4.1–4.45 (3H), 6.40 (2H), 6.9–7.1 (2H), 7.18 (1H), 7.32 (1H), 7.53 (1H), 7.70 (1H), 7.78 (1H), 7.83 (1H), 8.40 (1H), 9.42 (1H), 10.85 (1H)

LRMS: 755 (M+1)

Anal: C,H,N,S

EXAMPLE 68

N-[6-[6-[(benzyloxy)formamido]hexanamido] hexanoyl]-L-isoleucyl-L-isoleucine-L-N-[1-dimethoxymethyl]2-(1H-indol-3-yl)ethyl]amide Step 1: A solution of 5.3 g (20 mMol) of Cbz-6-aminohexanoic acid (Aldrich), 2.3 g (20 mMol) of N-hydroxysuccinimide, 4.8 g (25 mMol of EDCI, and 2.8 mL (20 mMol) of triethylamine in 100 mL of ethylacetate was stirred at 25° for 5 h. The mixture was diluted with ethylacetate and extracted with 1N aqueous hydrochloric acid and saturated aqueous sodium bicarbonate, dried over magnesium sulfate and concentrated in vacuo. The residue was redissolved in 50 mL of methanol and treated with 20 mL of water, 20 mL of ethyl acetate, 2.8 mL of triethylamine and 2.6 g of 6-aminohexanoic acid. The resulting mixture was stirred for 48 h at 25° and then concentrated in vacuo. The residue was diluted with ethyl acetate and extracted with 1N aqueous hydrochloric acid and dried over magnesium sulfate. The volatiltes were removed in vacuo and the residue was redissolved in 100 mL of ethyl acetate and 50 mL of tetrahydrofuran. 2.3 g of N-hydroxysuccinimide and 4.8 g of EDCI were added, followed by 5 mL of triethylamine, and the resulting mixture was stirred at 25° for 5 h. The reaction was diluted with ethyl acetate and extracted with 1N aqueous hydrochloric acid and saturated aqueous sodium bicarbonate, dried over magnesium sulfate and concentrated in vacuo, to give the desired activated ester (5.5 g) as a white solid.

Step 2: A solution of 0.8 g (1.73 mMol) of the free amine obtained in Step 1 of Example 58, 1.0 g (2 mMol) of the activated ester of Step 1 and 0.28 mL (2 mMol) of triethylamine in 20 mL of methanol was stirred at 25° for 1 h. 0.5 g of glycine were added and the mixture was stirred for an additional 1 h. The volatiles were removed in vacuo and the residue was partitioned between ethyl acetate and 1N aqueous hydrochloric acid. The organic layer was extracted with 1N aqueous sodium hydroxide and then saturated aqueous ammonium chloride, dried over magnesium sulfate, concentrated in vacuo and triturated with ether to afford the desired acetal (1.2 g) as a white solid.

1H-NMR (DMSO-$d_6$): Step 1: 1.2–1.6 (12H), 2.00 (2H), 2.63 (2H), 2.78 (4H), 2.97 (4H), 5.00 (2H), 7.20 (1H), 7.38 (5H), 7.75 (1H), Step 2: 0.75 (12H), 1.00 (2H), 1.2–1.5 (14H), 1.66 (2H), 2.00 (2H), 2.09 (2H), 2.75 (1H), 2.95 (4H), 3.23 (3H), 3.24 (3H), 4.18 (4H), 4.98 (2H), 6.97 (1H), 7.00 (2H), 7.38 (8H), 7.46 (1H), 7.65 (2H), 7.88 (1H), 10.72 (1H), LRMS Step 1: (476.5 (M+1) Step 2: 822 (M+1)

Anal: Step 1: C,H,N Step 2: C,H,N

EXAMPLE 69

N-[6-(6-[(1,2,3,6-tetrahydro-2,6-dioxo-4-pyrimidinyl)formamido]hexanamido]hexanoyl]-L-isoleucyl-L-isoleucine-L-N-[1-formyl]2-(1H-indol-3-yl)ethyl]amide Step 1: A solution of 1 g (1.2 mMol) of the compound obtained in Example 68 in 150 mL of methanol was treated with 0.1 g of 5% palladium on carbon and stirred under a hydrogen atmosphere at 25° for 2 h. The mixture was filtered through a bed of Celite and the volatiles were removed in vacuo. The residue was triturated with ether to give the free amine (0.85 g) as a white powder.

Step 2: A solution of 0.137 g (0.2 mMol) of the free amine of Step 1, 0.052 g (0.3 mMol) of orotic acid (Aldrich), 0.058 g (0.3 mMol) of EDCI, 0.044 g (0.3 mMol) of N-hydroxybenzotriazole in 1 mL of dimethylformamide was stirred at 25° for 12 h. The volatiles were removed in vacuo and the residue was partitioned between ethylacetate and 1N aqueous hydrochloric acid. The organic layer was washed with saturated aqueous sodium bicarbonate, dried over magnesium sulfate and concentrated in vacuo to give the crude acetal as a foam.

Step 3: The acetal obtained in Step 2 was converted to the desired aldehyde utilising a similar procedure to that described for Step 3 in Example 58. The aldehyde was obtained as an off-white solid (0.08 g).

1H-NMR (DMSO-$d_6$) Step 1: 0.78 (12H), 1.10 (2H), 1.2–1.6 (14H), 1.68 (2H), 2.03 (2H), 2.12 (2H), 2.85 (1H), 2.8–3.05 (5H), 3.36 (3H), 3.38 (3H), 4.18 (4H), 7.95–7.05 (3H), 7.30 (1H), 7.48 (1H), 7.65 (2H), 7.94 (1H), 10.72 (1H), Step 2: (CD3OD) 0.7–0.9 (12H), 1.15 (2H), 1.2–1.8 (16H), 2.18 (2H), 2.24 (2H), 2.8–3.2 (4H), 3.3 (2H, 3.38 (3H), 3.39 (3H), 4.19 (1H), 4.20 (2H), 4.38 (1H), 6.08 (1H), 6.95–7.1 (3H), 7.30 (1H), 7.57 (1H), Step 3: 0.78 (12H), 1.05 (2H), 1.2–1.8 (16H), 2.05 (2H), 2.17 (2H), 2.95–3.2 (6H), 4.20 (2H), 4.42 (1H), 5.99 (1H), 6.98 (1H), 7.05 (1H), 7.18 (1H), 7.35 (1H), 7.50 (1H), 7.70 (1H), 7.77 (1H), 7.83 (1H), 8.42 (1H), 8.78 (1H), 9.44 (1H), 10.68 (1H), 10.85 (1H), 11.27 (1H)

LRMS: Step 1: 688 Step 2: 826 Step 3: 780

EXAMPLE 70

N-[6-[6-2-(2,5-dioxo-4-imidazolidinyl)acetamido]] hexanamido]hexanoyl]-L-isoleucyl-L-isoleucine-L-N-[1-formyl]2-(1H-indol-3-yl)ethyl]amide Step 1: 0.047 g of hydantoinacetic acid was coupled to the free amine obtained in Step 1 of Example 69 according to the procedure used for Step 2 in example 69 to afford 0.025 g of the desired product as a beige solid. Step 2: The acetal obtained in Step 1 was converted to the aldehyde (0.01 g) using a protocol similar to the one utilised in Step 3 of Example 69

1HNMR (CD$_3$OD): Step 1: 0.78–0.95 (12H), 1.10 (2H), 1.2–1.6 (14H), 1.78 (2H), 2.17 (2H), 2.22 (2H), 2.59 (1H), 2.72 (1H), 2.84 (1H), 3.03 (1H), 3.15 (4H), 3.38 (3H), 3.40 (3H), 4.18 (3H), 4.37 (2H), 7.00 (3H), 7.34 (1H), 7.58 (1H), Step 2: 0.7–0.9 (12H), 1.15 (2H), 1.2–1.8 (16H), 2.18 (2H), 2.23 (2H), 2.5–3.1 (8H), 4.20 (2H), 4.37 (1H), 4.50 (1H), 6.9–7.1 (3H), 7.27 (1H), 7.58 (1H), LRMS Step 1: 828 Step 2: 782

Anal: Step 2: C,H,N

EXAMPLE 71

N-[6-(benzyloxy)carbonylaminohexanoyl]-L-isoleucyl-L-isoleucine-L-N[1-formyl]2-(1H-indol-3-yl)ethyl]amide Step 1: Cbz-6-aminohexanoic acid was coupled to the free amine (0.4 g) obtained in Step 1 of Example 58 using a protocol analogous to that used in Step 2 of Example 58 to give the desired acetal as a white solid.

Step 2: 0.1 g of the acetal obtained in Step 1 was converted to the aldehyde utilising a procedure similar to that used for Step 3 in Example 58 to give the desired compound as a light brown solid.

1H-NMR (DMSO-$d_6$): Step 1: 0.78 (12H), 1–1.8 (10H), 2.18 (2H), 2.79 (1H), 2.97 (3H), 3.37 (3H), 3.39 (3H), 4.02 (1H), 4.18 (3H), 5.02 (2H), 6.92–8.0 (14H), 10.84 (1H), Step 2: 0.78 (12H), 1.0–1.8 (10H), 2.17 (2H), 2.98 (3H), 3.20 (1H), 4.20 (2H), 4.42 (1H), 5.00 (2H), 6.95–8.0 (13H), 8.42 (1H), 9.46 (1H), 10.88 (1H), LRMS: Step 1: 708 Step 2: 662.5

Anal: Step 1: C,H,N Step 2: C,H,N

EXAMPLE 72

N-Pentanoyl-L-isoleucyl-L-isoleucine-L-N-[1-formyl]2-(1H-indol-3-yl)ethyl]amide

Step 1: A solution of 0.4 g (0.86 mMol), of the free amine obtained in Step 1 of Example 58 in 5 mL of pyridine was treated with 0.02 g of 4-dimethylaminopyridine and 0.13 g (1.08 mMol) of pentanoylchloride at 0°. The mixture was stirred at 25° for 12 h and the volatiles were removed in vacuo. The residue was partitioned between ethyl acetate and 1N aqueous hydrochloric acid. The organic layer was washed with saturated aqueous sodium bicarbonate, dried over magnesium sulfate and concentrated in vacuo to give the desired acetal (0.36 g) as a white solid.

Step 2: 0.1 g of the acetal from Step 1 were converted to the aldehyde (0.05 g white solid) utilising a protocol analogous to that used in Step 3 of Example 58.

1H-NMR (DMSO-d$_6$) Step 1 1: 0.6–0.85 (15H), 1.0–1.8 (10H), 2.17 (2H), 2.80 (1H), 2.95 (1H), 3.36 (3H), 4.20 (4H), 6.95–8.00 ((7H, 10.75 (1H), Step 2: 0.65–0.086 (15H), 1.00–1.80 (10H), 2.19 (2H), 3.22 (1H), 3.40 (1H), 4.20 (2H), 4.41 (1H), 6.95–8.00 (7H), 9.54 (1H), 10.72 (1H), LRMS Step 1: 545 Step 2: 499.5

Anal.: Step 1: C,H,N Step 2: C,H,N

EXAMPLE 73

N-[(3-methoxycarbonyl)propionyl]-L-isoleucyl-L-isoleucine-L-N-[1-dimethoxymethyl]2-(1H-indol-3-yl)ethyl]amide 3-N-methoxycarbonylpropionylchloride was coupled to 0.4 g of the free amine obtained in Step 2 of Example 58 using an analogous procedure to that outlined for Step 1 in Example 72 to give the dimethylacetal (0.39 g) as a white solid.

1H-NMR (DMSO-d$_6$) 0.78 (12H), 1.05 (2H), 1.38 (2H), 1.90 (2H), 2.44 (4H), 2.78 (1H), 2.96 (1H), 3.37 (6H), 3.58 (3H), 4.18 (4H), 6.60 (1H), 7.00 (3H), 7.38 (1H), 7.55 (1H), 7.75 (2H), 8.00 (1H), 10.73 (1H),

LRMS: 575

Anal.: C,H,N

EXAMPLE 74

N-[(3-methoxycarbonyl)propionyl]-L-isoleucyl-L-isoleucine-L-N[1-formyl]2-(1H-indol-3-yl)ethyl]amide 0.1 g of the acetal from Example 73 were converted to the aldehyde (0.05 g white solid) utilising a protocol analogous to that used in Step 3 of Example 58.

1H-NMR (DMSO-d$_6$): 0.78 (12H), 1.05 (2H), 1.40 (2H), 1.72 (2H), 2.42 (4H), 3.00 (1H), 3.20 (1H), 3.58 (3H), 4.20 (2H), 4.42 (1H), 7.01 (2H), 7.18 (1H), 7.38 (1H), 7.56 (1H), 7.80 (1H), 8.42 (1H), 9.44 (1H), 10.88 (1H),

LRMS: 529

Anal.: C,H,N

EXAMPLE 75

N-[benzyloxycarbonyl]-L-tryptophanyl-L-tryptophan-L-N-[1-semicarbazonomethyl]2-(1H-indol-3-yl)ethyl]amide Step 1: Boc-Tryptophan (60 g) was coupled with N,O-dimethylhydroxylamine using a protocol similar to that used for Step 2 of Example 58 to give Boc-Tryptophan-N,O-dimethylhydroxamide (52 g) as a white solid.

Step 2: 40 g of the amide of Step 1 were converted to the aldehyde using a procedure analogous to that used in Example 15 to give 30 g of Boc-Tryptophanal as a white solid.

Step 3: 7.0 g of Boc-Tryptophanal were converted to the semicarbazone (5.0 g, white solid) using a protocol analogous to that utilised in Example 56.

Step 4: 2.5 g (7.2 mMol) of the semicarbazone obtained in Step 3 were dissolved in 25 mL of dichloromethanbe and treated for 3 h with 24 mL of trifluoroacetic acid. The volatiles were removed in vacuo and the residue was coupled to Cbz-TrpTrp (Bachem Biosciences) using a protocol similar to that utilised in Step 2 of Example 58 to give the desired semicarbazone (1.5 g, white solid) after chromatography on silica gel (10% methanol/dichloromethane).

1H-NMR(DMSO-d$_6$) Step 3: 1.4 ((9H), 2.98 (2H), 4.38 (1H), 6.30 (1H), 7–7.6 (7H), 9.85 (1H), 10.8 (1H), Step 4: (CDCl$_3$): 3.2 (6H), 4.8 (3H), 5.00 (2H), 6.9–7.8 (20H)

LRMS: Step 4: 604 (M+Na)

Anal: C,H,N

EXAMPLE 76

N-[(benzyloxy)carbonyl]-L-aspart-1-yl]-L-isoleucyl-L-isoleucine-L-N-[1-dimethoxymethyl]2-(1H-indol-3-yl)ethyl]amide A solution of 0.1 g (0.13 mMol) of the acetal obtained in Step 1 of Example 64 in 10 mL of methanol was treated with 0.5 g of lithium hydroxide and stirred for 1 h at 25°. Ethyl acetate was added and the solution was extracted with 1N aqueous hydrochloric acid. Drying over magnesium sulfate and removal of the solvent in vacuo afforded the desired acid (0.1 g) as a beige solid.

1H-NMR(MeOH-d$_4$) 0.8 (12H), 1.15 (2H), 1.50 (2H), 1.85 (2H), 2.95 (2H), 3.05 (1H), 3.45 (3H), 3.50 (3H), 4.25 (3H), 4.42 (1H), 4.62 (1H), 5.20 (2H), 7.0–7.2 (3H), 7.4 (5H), 7.6 (1H)

LRMS: 711

EXAMPLE 77

N-Benzyloxycarbonyl-R-isoleucyl-S-isoleucine-1-S--formyl-2-(1H--indol-3-yl)-ethylamide The title compound was obtained in an analogous manner to the procedure outlined for Example 15, utilising a D-amino acid instead of an L-amino acid in the appropriate step of the sequence.

1H NMR (DMSO) δ: 0.63–0.93 (12H), 0.98–1.8 (4H), 2.62–3.07 (2H), 3.84–4.51 (3H), 5.06 (2H), 6.17–6.21 (1H), 6.31–6.36 (1H), 6.93–7.83 (10H), 8.48–8.57 (1H), 9.47 (1H), 10.63–10.84 (1H)

LRMS: (EI, m/e): 549 (M$^+$+1)

Anal. (1H$_2$O): C: 65.96, H: 7.60, N: 10.10

EXAMPLE 78

N-[[[5-(hexahydro-2-oxo-1H-thieno[3,4-d]imidazol-4-yl)valeramido]hexanoyl]-L-trytophanyl-L-tryptophan-L-N-[1-dimethoxymethyl]2-(1H-indol-3-yl)ethyl]amide 0.37 g of the dimethylacetal of TrpTrpTrp aldehyde, obtained using procedures similar to those utilised for the synthesis of the IleIleTrp analog described in Step 1 of Example 58 was biotinylated using the protocol outlined for Example 66 to give the desired product (0.4 g) as a white solid.

1H-NMR (DMSO-d$_6$): 1.0–1.8 (12H), 1.95 (2H), 2.58 (1H), 2.7–3.1 (13H), 3.37 (3H), 3.39 (3H), 4.12 (2H), 4.25 (1H), 4.5 (1H), 6.4 (2H), 6.96–8.00 (19H), 10.75 (2H), 10.80 (1H),

LRMS: 946 (M+1)

Anal: C,H,N,S

EXAMPLE 79

N-[12-[(benzyloxy)acetamido]dodecanoyl]--L-isoleucyl-L-isoleucine-L-N-[1-formyl]2-(1H-indol-3-yl)ethyl]amide 0.1 g of the desired compound was obtained from the free amine prepared in Step 1 of Example 58 and 12-Cbzamidododecanoic acid using the sequence utilised for Steps 2 and 3 of Example 58.

1H-NMR (CDCl$_3$) 0.8(12H)), 1.0–2.0 (24H), 2.20 (2H), 3.18 (4H), 4.37 (2H), 4.80 (2H), 5.08 (2H), 5.08 (2H), 7.0–7.6 (11H), 8.40 (1H), 9.58 (1H),

LRMS: 796 (M+2MeOH)

Anal: C,H,N

EXAMPLE 80

N-Benzyloxycarbonyl-L-isoleucyl-L-isoleucine-L-N [[1[acetoxyacetamido]2-(1H-indol-3-yl)ethyl]amide Step 1: Isobutylchloroformate (4.49 g, 36.2 mmol) was added dropwise to a stirring solution of Boc-(D or L)-Trp-OH (10.00 g, 32.9 mmol) in THF (120 ml) cooled to −10° C. The resulting white reaction mixture was stirred 15 min and filtered into a round bottom flask equipped with a stir bar. The stirring filtrate was cooled to −10° C. and TMSN$_3$ (6.6 ml, ca 49.4 mmol) was added dropwise and the solution stirred an additional 1.5 h at −10° C. The solution was concentrated at room temperature and the oil dissolved in EtOAc (150 ml). The EtOAc solution was washed with sat. NaHCO$_3$ (2×30 ml) and brine (2×30 ml), dried over MgSO$_4$, filtered and concentrated. The crude material was dissolved in toluene (200 ml) and the solution heated to 40° C. and maintained for 1 h. DABCO (0.52 g, 4.62 mmol) was added and the solution maintained at 40° C. for a additional 18 h. Concentration in vacuo and flash chromatography (silica gel;) 30% EtOAc/Hesanes) followed by crystallisation from Et$_2$O provided the title compound 1 (6.20 g, 15.1 mmol, 46% yield) as a white solid.

Step 2: A solution of the product of Step 1 (2.02 g, 4.93 mmol) in a mixture of MeOH (60 ml) and THF (10 ml) was hydrogenolyzed over Pd/C at 20 psi for 3 h. The mixture was filtered and concentrated to provide the free amine as an oil which was used immediately in the next step. A stirring solution of the free amine (4.93 mmol) in DMF (25 ml) was cooled in an ice bath and Z-lle-lle-OH (1.87 g, 4.93 mmol), EDCI (0.954 g, 4.93 mmol) and HOBT (0.666 gm 4.93 mmol) were added and the mixture stirred 3 h with gradual warming to room temperature. The deep red solution was concentrated in vacuo and the crude partitioned between EtOAc (75 ml) and 5% citric acid (25 ml). The layers were separated and the organic layer washed with sat. NaHCO$_3$ (2×25 ml) and brine (1×25 ml), dried over MgSO$_4$ filtered and concentrated. The crude material was purified by flash chromatography (silica gel: 50% EtOAc/Hexane) which provided the desired tripeptide (1.41 g, 2.05 mmol. 42% yield) as an off white solid: 50:50 mixture of diastereomers.

Step 3: A stirring mixture of the product obtained in Step 2 (211 mg, 0.332 mmol) in THF (1.1 ml) was cooled in an ice bath under N$_2$ atmosphere. Neat TFA (2 ml) was added slowly dropwise. The dark reaction mixture was stirred 1.5 h. The mixture was concentrated cold at reduced pressure and triturated with Et$_2$O. The resulting solid material (0.446 mmol), NMM (0.669 mmol), and acetoxy acetic acid (0.446 mmol) were dissolved in DMF (5 ml) and the solution cooled in an ice bath. EDCI (0.446 mmol) was added via spatula and the reaction mixture stirred for 3 h with warming to room temperature. The mixture was concentrated and the crude oil partitioned between EtOAc (10 ml) and 5% citric acid (5 ml). The layers were separated and the EtOAc layer washed with sat. NaHCO$_3$ (5 ml) and brine (5 ml), dried over M$_2$SO$_4$, filtered and concentrated, flash chromatography on silica gel (EtOAc/Hexane eluent) provided the title compound as a tan solid; 57.43 mixture of diastereomers;

Step 1: mp 132–133° C.;

1H NMR (DMSO-d$_6$) 10.81 (1H), 7.59 (2H), 7.33 (6H), 7.16 (1H), 7.06 (3H), 5.22 (1H), 5.01 (2H), 2.99 (2H), 1.36 (9H);

FAB-MS: 410 (M+1)

Step 2: 1H NMR (DMSO-d$_6$) 10.78 (1H), 8.13 (1H), 7.80 (1H), 7.60 (1H), 7.34 (7H), 7.05 (4H), 5.40 (1H), 5.05 (2H), 4.4–3.9 (2H), 2.95 (2H), 1.73 (2H), 1.6–0.9 (4H) 1.33 (9H), 0.8 (12H);

FAB MS 636 (M+1).

Step 3: 1H NMR (DMSO-d$_6$) 10.81 (1H), 8.24 (2H), 7.82 (1H), 7.60 (1H), 7.34 (7H), 7.15–6.90 (3H), 5.61 (1H), 5.04 (2H), 4.44, 4.38, 4.4–3.9 (2H), 3.04 (2H), 2.08, 2.05), 1.69 (2H) 1.42 (2H), 1.11 (2H), 0.80 (12H);

FAB MS: 636 (M+1)

EXAMPLE 81

N-(3-pyridylmethoxy)carbonyl-L-isoleucyl-L-isoleucine-L-N-[1-formyl]2-(1H-indol-3-yl)ethyl] amide Step 1: A solution of Cbz-lle-lle-Trp-N(Me)OMe obtained according to the procedures outlined in Examples 1–14, in THF (8 ml) and MeOH (20 ml) was hydrogenolyzed over 10% Pd—C (0.1 g) at 40 psi for 2 h. The mixture was filtered and concentrated to provide the free amine as a white solid.

Step 2: A solution of 3-pyridylcarbinol (0.207 g, 1.90 mmol) and triethyl amine (0.689 g, 6.81 mmol) in Et$_2$O (5 ml) was cooled in an ice bath and a solution of triphosgene (0.189 g, 0.637 mmol) in Et$_2$O (2 ml) was added dropwise. The resulting mixture was stirred for 30 min at 0° C. A solution of the free amine of Step 1 (0.200 g, 0.422 mmol) in THF (2 ml) wad added and the reaction mixture was allowed to warm to room temperature and stirred for 18 h. The reaction mixture was concentrated by rotovap and diluted with EtOAc. The EtOAc mixture was washed with brine, dried over MgSO$_4$ filtered and concentrated. Flash chromatography on silica gel eluting with 5% MeOH/ CH$_2$Cl$_2$ provided the desired amide as an off white solid. 93 mg (0.153 mmol) of which was dissolved in THF (3 ml), was cooled to −60° C. and LAH (100 mg, 2.64 mmol) was added slowly via spatula. The reaction mixture was stirred at −60° C. for 1.5 h, warmed to 0° C. and quenched with 10% citric acid. the mixture was basified to pH 10 with 1N NaOH and the THF was removed by rotovap. The aqueous mixture was extracted with EtOAc and the combined EtOAc layers were washed with H$_2$O and brine, dried over MgSO$_4$, filtered and concentrated, the resulting material was recrystallised from EtOAc/Hexane to provide the title compound as a white solid.

Step 1: FAB-MS: 474 (M+1)

Anal.: C,H,N

Step 2: FAB-MS: 550 (M+1)

Anal.: C,H,N

EXAMPLE 82

N-(benzloxy)carbonyl-L-isoleucyl-L-isoleucine-L-N-[1-[[[[3-(ethoxycarbonyl)-2-oxiranyl]carbonyl] amidolmethyl]-2-(1H-indol-3-yl)ethyl]amide Step 1: A solution of 2 g (5.6 mMol) of the mesylate obtained in Step 1 of Example 57 and 5 g of lithium azide in 25 mL of dimethylformide was heated to 100° for 3 h. The volatiles were removed in vacuo and the residue was partitioned between dichloromethane and water. The organic layer was dried over magnesium sulfate, concentrated in vacuo and chromatographed on silica gel (25%–40% ethylacetate/hexanes) to give the desired azide (0.8 g) as a white solid.

Step 2: 0.5 g (1.6 mMol) of the azide from Step 1 were dissolved in 15 mL of dichloromethane and treated with 10 mL of trifluoroacetic acid. The resulting mixture was stirred at 25° for 0.5 h and the volatiles were removed in vacuo. The residue was partitioned between dichloromethane and 1N aqueous sodium hydroxide. The organic layer was dried over magnesium sulfate and concentrated in vacuo, redissolved in 5 mL of dimethylformamide and treated with 1.32 g (3 mMol) of BOP and 0.945 g (2.5 mMol) of Cbz-lIelle (Bachem Bioscience), followed by 0.3 g (3 mMol) of N-methylmorpholine. The resulting mixture was stirred at 0° for 24 h, diluted with ethylacetate and extracted with 1N aqueous hydrochloric acid and saturated aqueous sodium bicarbonate. The organic layer was dried over magnesium sulfate, concentrated in vacuo and chromatographed on silica gel (50% ethylacetate/hexane) to give the tripeptide azide (0.8 g) as a white solid.

Step 3: A solution of 3.0 g (5.2 mmol) of the azide from Step 2 and 1.8 g (6.9 mmol) of $Ph_3P$ in a solvent mixture of $H_2O$ (1.6 mL), THF (30 mL) and $CH_3CN$ (30 mL) was stirred at room temperature overnight. The solution was evaporated in vacuo to dryness. The residue was chromatographed on a short silica gel pad eluted with EtOAc:hexane/ 1:1 followed by $CH_2Cl_2$:MeOH/9:1 to give 1.95 g of the desired amine as a white solid.

Step 4: To a solution of 0.2 g (0.36 mmol) of the amine obtained in Step 3 and 0.11 g (0.39 mmol) of trans-3-ethoxycarbonyloxiranylpropionic acid p-nitrophenylester in $CHCl_3$ (10 mL) was added 0.04 g (0.4 mmol) of triethylamine. After stirring at room temperature for 40 min, the reaction went to completion as determined by TLC. The resulting precipitate was filtered to give 0.106 solid of the desired product. The filtrate was washed with 0.1N NaOH, 0.1N HCl and $H_2O$, dried over $MgSO_4$ and evaporated in vacuo to give another 0.052 g of the desired compound as a solid (as a mixture of two diastereomers).

1H NMR Step 1: ($CDCl_3$) 0.41 (9H), 2.28 (2H), 3.38 (2H), 4.05 (1H), 4.7 (1H), 7.03 (1H), 7.1–7.3 (2H), 7.38 (1H), 7.64 (1H), 8.18 (1H), Step 2: ($CDCl_3$) 0.80 (12H), 1.11 (2H), 1.42 (2H), 1.85 (2H), 2.98 (2H), 3.38 (2H), 4.00 (1H), 4.20 (1H), 4.49 (1H), 4.98 (1H), 5.10 (2H), 5.3 (1H), 6.20 (1H), 6.40 (1H), 7–7.4 (10H), 7.60 (1H), 8.20 (1H).

Step 4: 0.6–0.9 (12H), 1.1 (3H), 1.21 (3H), 1.4 (1H), 1.7 (2H), 2.80 (2H), 3.3 (2H), 3.55 (1H), 3.61 (1H), 3.95 (1H), 4.1 (3H), 4.3 (1H), 5.00 (2H), 6.95 (1H), 7.05 (1H), 7.15 (1H), 7.30 (6H), 7.45 (1H), 7.55 (1H), 7.70 (1H), 7.85 (1H), 8.30 (1H), 10.80 (1H).

LRMS Step 1: 315, Step 2: 577, Step 4: 692

Anal. Step 1: C,H,N Step 2: C,H,N Step 3: C,H,N Step 4: C,H,N

EXAMPLE 83

N-(benzyloxy)carbonyl-L-isoleucyl-L-isoleucine-L-N-[1-[(3-maleimidopropionamido]methyl]-2-(1H-indol-3-yl)ethyl]amide A solution of 0.1 g (0.18 mmol) of the amine obtained in Step 3 of Example 82 and 0.75 g (0.28 mmol) of 3-maleiimidopropionic acid hydroxysuccimideester in $CH_2Cl_2$ (5 mL) was stirred at room temperature. To this solution was added 0.02 g (0.2 mmol) of triethylamine. After stirring for 2 h the resulting precipitate was filtered to give 0.057 g of the desired compound as a solid.

1H NMR (DMSO-$d_6$) δ 0.6–0.8 (12H), 0.95 (1H), 1.15 (2H), 1.4 (1H), 1.70 (2H), 2.35 (2H), 2.75 (2H), 3.1 (1H), 3.2 (1 H), 3.60 (2H), 4.00 (2H), 4.05 (1H), 4.25 (1H), 5.02 (2H), 6.95 (1H), 6.96 (2H), 7.00 (1H), 7.05 (1H), 7.31 (6H), 7.40 (1H), 7.55 (1H), 7.65 (1H), 7.85 (1H), 7.90 (1H).

LRMS: (FAB) m/e 701 (M+1)

Anal: C,H,N

EXAMPLE 84

N-(benzyloxy)carbonyl-L-isoleucyl-L-isoleucine-L-N-[(2-maleimidoacetamido]methyl]-2-(1H-indol-3-yl)ethyl]amide A solution of 0.2 g (0.36 mmol) of the amine obtained in Step 3 of Example 82, 0.06 g (0.40 mmol) of maleimidoacetic acid (*J. Med. Chem.* 1975, 18, 1004), 0.08 g (0.79 mmol) of N-methylmorpholine. 0.056 g (0.41 mmol) of hydroxybenzotriazole and 0.076 g (0.40 mmol) of EDCl in DMF (5 mL) was stirred at room temperature overnight. The solution was evaporated in vacuo. The residue was partitioned between EtOAc and saturated aqueous $NaHCO_3$. The separated EtOAc solution was washed with 1N HCl and then $H_2O$, dried over $MgSO_4$ and evaporated in vacuo to dryness. Recrystallisation of the residue from THF/$Et_2O$ gave 0.13 g of the title compound.

1H NMR (DMSO-$d_6$) δ 0.65–0.85 (12h), 1.1 (2H), 1.4 (2H), 1.7 (2H), 2.75 (2H), 3.05–3.20 (2H), 3.9–4.2 (5H), 5.03 (2H), 6.95 (1H), 7.08 (1H), 7.09 (2H), 7.25–7.35 (7H), 7.55 (1H), 7.8 (2H), 8.1 (1H).

LRMS: (FAB) m/e 687 (M+1)

Anal: C,H,N

EXAMPLE 85

N-(benzyloxy)carbonyl-L-isoleucyl-L-isoleucine-L-N-[1-[(2-chloroacetamido]methy]-2-(1H-indol-3-yl)ethyl]amide A solution of 0.15 g (0.26 mmol) of the free amine obtained in Step 3 of Example 82, 0.2 g (1.8 )mmol) chloroacetyl chloride and 0.3 g (2.2 mmol) of potassium carbonate in $CHCl_3$ (5 mL) was stirred at room temperature for 1 h. After filtration of the insoluble material, the $CHCl_3$ solution was evaporated in vacuo to dryness. The residue was stirred in $Et_2O$ and filtered to give 0.087 g of the title compound.

1H NMR (DMSO-$d_6$) δ 0.6–0.8 (12H), 1.15 (1H), 1.4 (1H), 1.70 (1H), 2.80 (2H), 3.20 (2H), 3.9 (1H), 4.03 (2H), 4.1 (1H), 4.3 (1H), 5.02 (2H). 6.9 (1H), 7.05 (1H), 7.15 (1H), 7.31 (6H), 7.4 (1H), 7.55 (1H), 7.8 (2H), 8.1 (1H).

LRMS: (FAB) m/e 626 (M+1)

Anal: CHNCl

EXAMPLE 86

N-(benzyloxy)carbonyl-L-isoleucyl-L-isoleucine-L-N-[1-[(2-hydroxyacetamido]methyl]-2-(1H-indol-3-yl)ethyl]amide Step 1: A mixture of 0.55 g (1 mmol) of the free amine obtained in Step 3 of Example 82, 1.5 g (11 mmol) of acetoxyacetyl chloride and 2 g (1 mmol) of potassium carbonate in CHCl₃ (60 mL) was stirred at room temperature for 1½ h. H₂O (20 mL) was added. The CHCl₃ solution was separated dried over MgSO₄ and evaporated in vacuo to dryness. The residue was chromatographed on silica gel with CHCl₃ followed by 5% MeOH in CHCl₃ to give 0.22 g of the desired acetoxy compound.

Step 2: To a solution of 0.033 g (0.6 mmol) of NaOMe in MeOH (5 mL) was added 0.4 g (0.6 mmol) of the acetoxy compound obtained in Step 1. After stirring at room temperature for 1 h, the solution was neutralised with 1N HCl. The mixture was evaporated to almost dryness and the residue was partitioned between EtOAc and H₂O. The EtOAc solution was dried over MgSO₄ and evaporated in vacuo to give 0.2 g of the title compound.

1H NMR (DMSO-$d_6$) Step 1: 1H NMR (DMSO-$d_6$) δ 0.6–0.8 (12H), 1.1 (2H), 1.1 (2H), 1.4 (2H), 1.7 (2H), 2.50 (3H), 2.75 (2H), 3.15 (2H), 3.95 (1H), 4.1 (1H), 4.25 (1H), 4.40 (2H), 5.00 (2H), 6.95 (1H), 7.15 (1H), 7.33 (6H), 7.55–7.95 (5H). Step 2: 0.63–0.85 (12H), 1.1 (2H), 1.4 (2H), 1.7 (2H), 2.8 (2H), 3.15 (2H), 3.75 (2H), 4.0 (1H), 4.1 (1H), 4.3 (1H), 5.0 (2H), 5.45 (1H), 6.95 (1H), 7.05 (1H), 7.15 (1H), 7.33 (6H), 7.45–8.00 (5H).

LRMS: Step 1: 650 (M+1) Step 2: 608 (M+1)
Anal. Step 1: C,H,N Step 2: C,H,NCHN

EXAMPLE 87

N-[[[5-(hexahydro-2-oxo-1H-thieno[3,4-d]imidazol-4-yl)valeramido]hexanoyl]-L-tryptophanyl-L-tryptophan-L-N-[1-semicarbazonomethyl]2-(1H-indol-3-yl)ethyl]amide The product of Step 4 of Example 75 was converted to the free amine using a protocol analogous to that used in Step 1 of Example 58 and then coupled to the N-hydroxysuccinimid ester of biotinylamidocaproic acid using a procedure similar to that used in Example 66 to give the desired product as a white solid (0.22 g)

1H-NMR (DMSO-$d_6$): 1.0–1.6 (14H), 2.03 (4H), 2.7–3.2 (13H), 4.06 (1H), 4.30 (1H), 4.60 (2H), 6.40 (2H), 6.8–8.2 (20H), 9.90 (1H), 10.80 (3H),

LRMS: 974.5 (M+NH₄)
Anal: C,H,N,S

EXAMPLE 88

N-Benzyloxycarbonyl-L-isoleucyl-L-isoleucine-L-N-[1-oxalyl]2-(phenyl)ethyl]amide A solution of 0.3 g (0.52 mMol) of the ethylester obtained in Example 53 in 3 mL of methanol was treated with 0.65 mL of 1N aqueous sodium hydroxide. The resulting suspension was stirred for 3 h at 25° and the now clear solution was diluted with ethyl acetate. Extraction with 1N aqueous hydrochloric acid and saturated aqueous ammonium chloride, followed by drying and removal of the solvent in vacuo, afforded a gum which was triturated with ether to give the desired acid (0.2 g) as a white solid.

1H-NMR (DMSO-$d_6$): 0.55–0.9 (12H), 1.05 ( ), 1.38 (2H), 1.67 (2H), 2.78 (1H), 3.06 (1H), 3.88 (1H), 4.221H), 4.85 (1H), 5.00 (2H), 7.05–7.4 (11H), 7.63 (1H), 8.55 (1H)

LRMS: 555 (M+1)
Anal: C,H,N

EXAMPLE 89

N-(5-phenylpentanoyl)-L-isoleucyl-L-isoleucine-L-N-[1-formyl]2-(1H-indol-3-yl)ethyl]amide This compound was obtained following procedures utilised for Example 59 and starting with commercially available (Aldrich) 5-phenylpentanoic acid.

1H-NMR (DMSO-$d_6$): 0.88 (12H), 1.3–1.9 (12H), 2.18 (2H), 3.00 (1H), 3.20 (1H), 4.20 (2H), 4.40 (1H), 6.98–7.98 (13H), 9.48 (1H), 10.88 (1H)

LRMS: 575.5 (M+H)
Anal: C,H,N

EXAMPLE 90

N-(3-phenoxypropionyl)l-L-isoleucyl-L-isoleucine-L-N-[1-formyl]2-(1H-indol-3-yl(ethyl]amide This compound was obtained following the procedures utilised for Example 59 and starting with commercially available (Aldrich) 3-Phenoxypropanoic acid.

1H-NMR(DMSO-$d_6$): 0.84 (12H), 1.04 (2H), 1.40 (2H), 1.70 (2H), 2.60 (2H), 3.00 (1H), 3.20 (1H), 4.1–4.4 (5H), 6.8–7.4 (9H), 7.55 (1H), 7.84 (1H), 8.04 (1H), 8.44 (1H), 9.50 (1H), 10.88 (1H)

LRMS: 563.5 (M+H)
Anal: C,H,N

EXAMPLE 91

N-[[5-(hexahydro-2-oxo-1H-thieno[3,4-d]imidazol-4-yl)pentanoyl]-L-tryptophanyl-L-tryptophan-L-N-[1-formyl]2-(1H-indol-3-yl)ethyl]amide A solution of 0.9 g (0.77 mMol) of Cbz-Trp Trp Trp-N, O-dimethylhydroxamide obtained according to the general procedures outlined above, in 150 mL of methanol was treated with 0.1 g of 5% palladium on Charcoal and stirred under an atmosphere of hydrogen gas for 4 h. The mixture was filtered through a bed of Celite and the volatiles were removed in vacuo to give 0.45 g of a colorless oil, which was redissolved in 5 mL of pyridine and treated with 0.33 g (0.89 mMol) of biotin-p-nitrophenylester and 0.05 g of dimethylaminopyridine. The resulting mixture was stirred for 12 h and the volatiles were removed in vacuo. The residue was partitioned between ethyl acetate and 1N aqueous hydrochloric acid, the organic layer was washed with aqueous sodium bicarbonate, dried and concentrated in vacuo to give 0.37 g of the desired amide as a yellow solid). 2 g (0.26 mMol) of this material was dissolved in 10 mL of tetrahydrofuran and cooled to −78°. The resulting mixture was treated with 0.5 mL of 1N lithium aluminum hydride in tetrahydrofuran and stirred at −40° for 12 h. Quenching the reaction with 100 mL of 1N aqueous sodium bisulfate, followed by extraction with ethyl acetate and washing of the organic layer with saturated aqueous sodium bicarbonate afforded the crude aldehyde after concentration in vacuo. Purification on silica gel (5% methanoldichloromethane) afforded 0.08 g of the desired product as a pale yellow solid.

LRMS: 787
Anal: C,H,N,S

EXAMPLE 92

N-[[5-(hexahydro-2-oxo-1H-thieno[3,4-d]imidazol-4-yl)pentanoyl]-L-p-bromophenylalanyl-L-1-naphthylalanyl-L-N-[1-dimethoxymethyl]2-(1H-indol-3-yl)ethyl]amide A solution of p-bromophenylalanyl-1-naphthylalanine 1 g (2.3 mMol), obtained according to the general procedures outlined above, and 1.2 g (11.3 mMol) of potassium carbonate in 20 mL of water was cooled to 0° and treated dropwise with a solution of N-hydroxysuccinimide biotin in 10 ml of 1,4-dioxane. The resulting mixture was stirred at 25° for 12 h and then acidified to pH2 with 1N aqueous hydrochloric acid. The precipitate was collected and washed with water. Drying in vacuo afforded the desired acid as a white solid (1.05 g). 1.25 g (0.37 mMol) of this intermediate were dissolved in 25 mL of dimethylformamide and treated with 0.09 g (0.37 mMol) of tryptophandimethylacetal, 0.07 g (0.37 mMol) of EDCI and 0.05 g (0.37 mMol) of N-hydroxybenzotriazole. The mixture was stirred at 25° for 12 h and concentrated in vacuo. The residue was partitioned between ethylacetate and 1N aqueous hydrochloric acid and the organic layer was washed with saturated aqueous sodium bicarbonate, dried and concentrated in vacuo. Chromatography on silica gel (8% methanol-dichloromethane) afforded the desired acetal as a white solid.

LRMS: 884

Anal: C,H,N,S

EXAMPLE 93

N-[[5-(hexahydro-2-oxo-1H-thieno[3,4-d]imidazol-4-yl)pentanoyl]-L-p-bromophenylalanyl-L-1-naphthylalanyl-L-N-[1-formyl]2-(1H-indol-3-yl)ethyl]amide 1 g of the acetal obtained in Example 92 were converted to the aldehyde (0.01 g white solid) according to the procedure outlined for Step 3 in Example 58

LRMS: 837/839

EXAMPLE 94

N-(benzyloxy)carbonyl-L-p-bromophenylalanyl-L-1-naphthylalanyl-L-N-[1-[2-oxiranylcarbonyl]]2-phenylethyl]amide Step 1: A solution of 11 g of Boc-phenylalanine-N,O-dimethylhydroxamide in 250 mL of tetrahydrofuran was treated with 250 mL of 1N vinylmagnesium bromide in tetrahydrofuran and the resulting mixture was stirred at 25° for 1 h. The reaction was quenched with 1N aqueous hydrochloric acid and extracted with ethyl acetate. The organic layer was dried, concentrated and filtered through a bed of silica gel with 25% ethylacetate-hexanes. Trituration with methyltert.butylethrt/hexanes (1:10) afforded the desired vinylketone 8 g) as a white solid. 7 g of this material were dissolved in 200 mL of methanol and treated with 9 g of cerium-lll-chloride heptahydrate, followed by 2 g of sodium borohydride. The mixture was diluted with ethyl acetate and extracted with saturated aqueous ammonium chloride. Drying and concentration in vacuo, followed by trituration with 10% ether.hexane afforded the desired alcohol as a 2:1 mixture of diastereomers (5 g, white solid) which was dissolved in 50 mL of 4M hydrogen chloride in 1,4-dioxane. The resulting solution was kept at 25° for 1 h and the volatiles were removed in vacuo. The residue was partitioned between ethylacetate and saturated aqueous sodium bicarbonate and the organic layer was dried and concentrated in vacuo to give the crude amino alcohol as a brown oil (2 g).

Step 2: A solution of biotinyl-p-bromophenylalanyl-1-naphthylalanine as obtained in Example 93 (1.0 g, 1.8 mMol) in 25 mL of dimethylformamide was treated with 0.38 g (2.2 mMol) of the aminoalcohol obtained in Step 1, 0.41 g (2.2 mMol) of EDCI and 0.34 g (2.2 mMol) of N-hydroxybenzotriazole. The resulting mixture was stirred at 25° for 12 h and concentrated in vacuo. Trituration with ether afforded the desired alcohol as a white solid (1.1 g). 0.7 g (1 mMol) of this compound were redissolved in 100 mL of chloroform and treated with 2.5 g (15 mMol) of m-chloroperbenzoic acid. The mixture was stirred at 25° for 15 h and extracted with 1N aqueous sodium hydroxide. Drying and concentration in vacuo afforded the desired epoxide as a white solid (0.8 g). An aliquot (0.2 g) of this compound was redissolved in 5 mL of dimethylsulfoxide and treated with 1.3 mL of acetic anhydride. The mixture was allowed to stand for 4 days and was then diluted with water. The precipitate was collected and washed with water. Chromatography on silica gel (5% methanol/dichloromethane) gave the desired ketoepoxide as a ca 2:1 mixture of diastereomers at the epoxide center. Further chromatography separated the diastereomers to produce two white solids (~0.01 g each).

LRMS: diastereomer 1: 748/750 diastereomer 2: 748/750

EXAMPLE 95

N-[(benzyloxy)carbonyl]-L-isoleucyl-L-isoleucine-L-N-[1-(N-maleimidomethyl)-2-(1H-indol-3-yl)ethyl]amide Step 1. To a solution of 0.55 g (1 mmol) of the amine obtained in Step 3 of Example 82 in THF (25 mL) was added 0.108 g (1.1 mmol) of maleic anhydride. The resulting solution was stirred at room temperature overnight. Dilution with diethyl ether (75 mL) followed by filtration of the resulting precipitate gave 0.17 g of the desired amide as a yellow solid. The filtrate was further concentrated to give an additional 0.4 g of the product.

Step 2. To a solution of 50 mg (0.08 mmol) of the intermediate from Step 1, 5 mg (0.04 mmol) of DMAP and 0.3 mL of pyridine in THF (5 mL), pre-cooled at −30° C. and under $N_2$, was added 0.2 mL (1.6 mmol) of cyanuric fluoride. The resulting solution was stirred at this temperature for 1 h and then allowed to warm to room temperature overnight. The mixture was partitioned between EtOAc and 1N HCl. The organic layer was separated, washed with $H_2O$, dried over $MgSO_4$ and evaporated to dryness. The residue was chromatographed on preparative TLC plate eluted with $CHCl_3$:MeOH/95:5. The desired band was extracted with THF. Evaporation of the solvent gave 2 mg of the title compound as a solid.

Step 1: 1H NMR (DMSO-$d_6$) 0.6–0.8 (12H), 1.1 (2H), 1.4 (2H), 1.7 (2H), 2.9 (2H), 3.1–3.4 (4H), 3.95 (1H), 4.2 (2H), 5.0 (2H), 6.2 (1H), 6.3 (1H), 6.95 (1H), 7.0 (1H), 7.15 (1H), 7.3 (6H), 7.6 (1H), 7.8 (1H), 7.9 (1H), 10.8 (1H)

LRMS: 665 (M+NH4)

Anal: C,H,N

Step 2: 1H NMR (DMSO-$d_6$): 0.65–0.85 (12H), 1.1–1.6 (6H), 3.2–3.4 (4H), 3.5 (2H), 3.9 (2H), 4.1 (1H), 5.0 (2H), 6.85 (1H), 6.93 (2H), 7.0 (1H), 7.1 (1H), 7.3 (6H), 7.5 (1H), 7.65 (2H), 7.9 (1H), 8.0 (1H)

LRMS: 630 (M+1)

EXAMPLE 96

N-[(benzyloxy)carbonyl]-L-isoleucyl-L-isoleucine-L-N-[1-(3-methoxycarbonyloxalyl]2-(phenyl)ethyl]amide Step 1: A mixture of 2.75 g (5.2 mmol) of CBZ-IIellePhe, assembled using the general procedures outlined above, 1.92 g (5.7 mmol) of methyltriphenylphosphoranylideneacetate (Aldrich), 1.0 g (5.2 mmol) of EDCI and 60 mg (0.5 mmol) of 4-DMAP in $CH_2Cl_2$ (200 mL) was stirred to dissolve gradually at room temperature overnight. The resulting solution was washed with 1N HCl and then saturated aqueous NaHCO$_3$. The solution was dried over MgSO$_4$ and evaporated to dryness. The residue was chromatographed on silica gel eluted with CHCl$_3$ followed by CHCl$_3$:EtOAc/9:1 to give 1.7 g of the desired phosphorane as a solid.

Step 2: A mixture of 0.33 g (0.4 mmol) of the phosphorane obtained in Step 1 and 1.0 g (1.2 mmol) of oxone in THF/H$_2$O (10 mL/8 mL) was stirred at room temperature overnight. The mixture was partitioned between EtOAc and H$_2$O. The organic layer was separated, dried over MgSO$_4$ and evaporated to dryness. The residue was stirred in diethyl ether and sonicated. The insoluble white solid was filtered to give 0.038 g of the title compound as a white solid.

Step 1: 1H NMR (DMSO-d$_6$) 0.5–0.7 (12H), 1.0 (2H), 1.3 (2H), 1.6 (2H), 2.6 (1H), 2.96 (3H), 3.2 (1H), 3.85 (1H), 4.1 (1H), 5.0 (2H), 5.75 (1H), 7.1–7.2 (5H), 7.3 (5H), 7.5–7.6 (15H), 7.7 (1H), 7.8 (1H)

LRMS: 842 (M+1)

Anal: C,H,N,P

Step 2: 1H NMR (DMSO-$_6$): 0.5–1.0 (12H), 1.05 (2H), 1.35 (2H), 1.6 (2H), 2.8–3.1 (2H), 3.53 (3H), 3.9 (1H), 4.2 (1H), 4.45 (1H), 5.0 (1H), 7.2 (5H), 7.3 (5H), 7.7 (1H), 8.4 (1H)

LRMS: 596 (M+1)

EXAMPLE 97

N-Benzyloxycarbonyl-S-cyclohexylalanyl-S-(O-benzyl)tyrosyl-1-S-formyl-1-(4-bromophenylmethyl)-methylamide 1H NMR (δ, DMSO-d$_6$): 0.6–1.7 (11H), 2.6–3.2 (6H), 4.0–4.6 (3H), 5.0 (4H), 6.8–7.5 (19H), 8.0 (1H), 8.5 (1H), 9.3 (1H)

LRMS: (Ion Spray): 768.3 (MH$^+$)

EXAMPLE 98

N-Benzyloxycarbonyl-S-(O-benzyl)tyrosyl-S-(O-benzyl)tyrosyl-1-S-formyl-1-(4-bromophenylmethyl)-methylamide 1H NMR (δ, DMSO-d$_6$): 2.6–3.2 (6H), 4.2 (2H), 4.5 (1H), 5.0 (6H), 6.8–7.5 (28H), 8.2 (1H), 8.6 (1H), 9.3 (1H)

LRMS: (Ion Spray): 868.2 (MH$^+$)

EXAMPLE 99

N-Benzyloxycarbonyl-S-(O-benzyl)tyrosyl-S-(O-ethyl)tyrosyl-1-S-formyl-1-(4-bromophenylmethyl)-methylamide 1H NMR (δ, DMSO-$_6$): 2.6–3.2 (6H), 3.9 (2H), 4.2 (2H), 4.5 (1H), 5.0 (4H), 6.7–7.5 (23H), 8.2 (1H), 8.6 (1H), 9.3 (1H)

LRMS: (Ion Spray): 806.4 (MH$^+$)

EXAMPLE 100

N-Benzyloxycarbonyl-S-(O-ethyl)tyrosyl-S-(O-benzyl)tyrosyl-1-S-formyl-1-(4-bromophenylmethyl)-methylamide 1H NMR (δ, DMSO-d$_6$): 1.4 (3H), 2.4–3.0 (6H), 4.0 (2H), 4.2 (1H), 5.0 (5H), 5.1 (1H), 6.7–7.6 (23H), 8.2 (1H), 8.6 (1H), 9.3 (1H)

LRMS: (Ion Spray): 806.4 (MH$^+$)

EXAMPLE 101

IC$_{50}$ values were determined as follows:

Porcine Aortic "ECE" Prep

Porcine aortas (22–25) were obtained fresh from a local slaughterhouse and delivered in cold PBS on ice. The aortas were cut open, rinsed with cold PBS and the endothelial cell layer scraped into cold PBS using a scalpel. The endothelial cells were pelleted by centrifugation, rinsed once with cold PBS, and repelleted. The pellet was lysed by addition of 10 volumes of 10 mM Tris-HCl, pH 7.0, containing protease inhibitors and DTS, followed by brief sonication and homogenization. The lysate was centrifuged at 100,000 g for 1 hour and the supernatant applied to a MONOQ FPLC anion exchange column equilibrated in 10 mM Tris-HCl, pH 7.0 (buffer A) which was then developed with an increasing gradient of NaCl in buffer A. The active fractions were aliquoted and stored at −70° C.

"ECE" Assay

The ECE assay was performed in 96-well microplates in a total volume of 200μ/well. The assay cocktail contains 100 mM Tris-HCl, pH 7.0, 20 mM CaCl$_2$, 80 μM substrate (Suc-Ile-Ile-Trp-MCA), enzyme and test compounds. The test compounds were preincubated with the enzyme for 15–20 minutes before initiation of the assay by addition of the substrate. The assay was incubated overnight at 37° C. and the fluorescence intensity caused by the release of AMC was determined using a fluorescence microplate reader (EX360 nm/EM460 nm). IC$_{50}$ values for compounds were determined by constructing concentration-effect curves for the inhibition of enzyme activity. Concentrations on the linear portion of the inhibition curve were used to determine the IC$_{50}$ utilizing a Hill plot.

| Compounds | Results IC$_{50}$ (lm) |
|---|---|
| Example 15 | IC$_{50}$ (μM) = 0.2 |
| Example 16 | IC$_{50}$ (μM) = 0.4 |
| Example 17 | IC$_{50}$ (μM) = 4.4 |
| Example 18 | IC$_{50}$ (μM) = 0.6 |
| Example 19 | IC$_{50}$ (μM) = 0.01 |
| Example 20 | IC$_{50}$ (μM) = 1.1 |
| Example 21 | IC$_{50}$ (μM) = 1.2 |
| Example 22 | IC$_{50}$ (μM) = 4.0 |
| Example 23 | IC$_{50}$ (μM) = 3.5 |
| Example 24 | IC$_{50}$ (μM) = 1.5 |
| Example 25 | IC$_{50}$ (μM) = 0.3 |
| Example 26 | IC$_{50}$ (μM) = 1.5 |
| Example 27 | IC$_{50}$ (μM) = 0.5 |
| Example 28 | IC$_{50}$ (μM) = 0.2 |
| Example 29 | IC$_{50}$ (μM) = 0.2 |
| Example 30 | IC$_{50}$ (μM) = 0.2 |
| Example 31 | IC$_{50}$ (μM) = 0.06 |
| Example 32 | IC$_{50}$ (μM) = 0.1 |
| Example 33 | IC$_{50}$ (μM) = 0.2 |
| Example 34 | IC$_{50}$ (μM) = 0.008 |
| Example 35 | IC$_{50}$ (μM) = 0.03 |
| Example 36 | IC$_{50}$ (μM) = 0.03 |
| Example 37 | IC$_{50}$ (μM) = 0.007 |
| Example 38 | IC$_{50}$ (μM) = 0.008 |
| Example 39 | IC$_{50}$ (μM) = 0.015 |
| Example 40 | IC$_{50}$ (μM) = 0.01 |
| Example 41 | IC$_{50}$ (μM) = 1.6 |
| Example 42 | IC$_{50}$ (μM) = 8 |
| Example 43 | IC$_{50}$ (μM) = 2 |
| Example 44 | IC$_{50}$ (μM) = 10 |

-continued

Results

| Compounds | IC$_{50}$ (lm) |
|---|---|
| Example 45 | IC$_{50}$ ($\mu$M) = 0.2 |
| Example 46 | IC$_{50}$ ($\mu$M) = 0.8 |
| Example 47 | IC$_{50}$ ($\mu$M) = 5 |
| Example 48 | IC$_{50}$ ($\mu$M) = 10 |
| Example 49 | IC$_{50}$ ($\mu$M) = 10 |
| Example 50 | IC$_{50}$ ($\mu$M) = 2 |
| Example 51 | IC$_{50}$ ($\mu$M) = 10 |
| Example 52 | IC$_{50}$ ($\mu$M) = 2 |
| Example 53 | IC$_{50}$ ($\mu$M) = 10 |
| Example 54 | IC$_{50}$ ($\mu$M) = 10 |
| Example 55 | IC$_{50}$ ($\mu$M) = 8 |
| Example 56 | IC$_{50}$ ($\mu$M) = 10 |
| Example 57 | IC$_{50}$ ($\mu$M) = 1 |
| Example 58 | IC$_{50}$ ($\mu$M) = 0.1 |
| Example 59 | IC$_{50}$ ($\mu$M) = 0.1 |
| Example 60 | IC$_{50}$ ($\mu$M) = 1 |
| Example 61 | IC$_{50}$ ($\mu$M) = 0.8 |
| Example 62 | IC$_{50}$ ($\mu$M) = 2 |
| Example 63 | IC$_{50}$ ($\mu$M) = 0.03 |
| Example 64 | IC$_{50}$ ($\mu$M) = 0.06 |
| Example 65 | IC$_{50}$ ($\mu$M) = 0.1 |
| Example 66 | IC$_{50}$ ($\mu$M) = 0.3 |
| Example 67 | IC$_{50}$ ($\mu$M) = 0.08 |
| Example 68 | IC$_{50}$ ($\mu$M) = 5 |
| Example 69 | IC$_{50}$ ($\mu$M) = 0.06 |
| Example 70 | IC$_{50}$ ($\mu$M) = 0.08 |
| Example 71 | IC$_{50}$ ($\mu$M) = 0.04 |
| Example 72 | IC$_{50}$ ($\mu$M) = 0.15 |
| Example 73 | IC$_{50}$ ($\mu$M) = 8 |
| Example 74 | IC$_{50}$ ($\mu$M) = 0.08 |
| Example 75 | IC$_{50}$ ($\mu$M) = 0.04 |
| Example 76 | IC$_{50}$ ($\mu$M) = 2.6 |
| Example 77 | IC$_{50}$ ($\mu$M) = 1 |
| Example 78 | IC$_{50}$ ($\mu$M) = 10 |
| Example 79 | IC$_{50}$ ($\mu$M) = 0.06 |
| Example 80 | IC$_{50}$ ($\mu$M) = 10 |
| Example 81 | IC$_{50}$ ($\mu$M) = 0.2 |
| Example 82 | IC$_{50}$ ($\mu$M) = 10 |
| Example 83 | IC$_{50}$ ($\mu$M) = 1 |
| Example 84 | IC$_{50}$ ($\mu$M) = 1 |
| Example 85 | IC$_{50}$ ($\mu$M) = 10 |
| Example 86 | IC$_{50}$ ($\mu$M) = 10 |
| Example 87 | IC$_{50}$ ($\mu$M) = 0.06 |
| Example 88 | IC$_{50}$ ($\mu$M) = 0.6 |
| Example 89 | IC$_{50}$ ($\mu$M) = 0.05 |
| Example 90 | IC$_{50}$ ($\mu$M) = 0.06 |
| Example 91 | IC$_{50}$ ($\mu$M) = 0.005 |
| Example 92 | IC$_{50}$ ($\mu$M) = 1 |
| Example 93 | IC$_{50}$ ($\mu$M) = 0.002 |
| Example 94 | IC$_{50}$ ($\mu$M) = 0.006 |
| Example 95 | IC$_{50}$ ($\mu$M) = 1 |
| Example 96 | IC$_{50}$ ($\mu$M) = 10 |
| Example 97 | IC$_{50}$ ($\mu$M) = 10 |
| Example 98 | IC$_{50}$ ($\mu$M) = 1 |
| Example 99 | IC$_{50}$ ($\mu$M) = 0.02 |
| Example 100 | IC$_{50}$ ($\mu$M) = 0.06 |

What is claimed is:

1. A compound of the formula (I) or a salt thereof

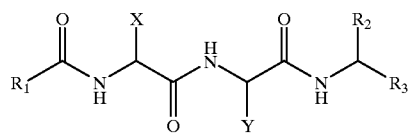

I wherein:

$R_1$ is $C_{5-7}$aryl, $C_{5-7}$arylC$_{1-7}$alkyl, $C_{5-7}$arylC$_{1-4}$alkoxy, $C_{5-7}$aryloxyC$_{1-4}$ alkyl, carboxyC$_{1-4}$alkyl, $C_{1-4}$alkoxycarbonylC$_{1-4}$alkyl, $C_4$alkyl or di-phenylC$_{1-4}$alkyl, such aryl groups or aryl moieties or aryl-containing groups being optionally substituted with $C_{1-4}$alkyl, halo, nitro, carboxyl or sulphonyl, or $R_1$ is a group of formula IIa, IIb, or IIc:

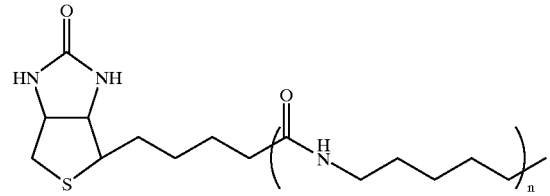

IIa

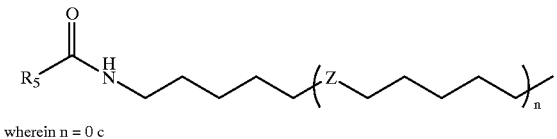

IIb wherein n = 0 c wherein n=0 or 1 and Z is —CONH— or —CH$_2$— and $R_5$ is benzyloxy, 2,3,6-tetrahydro-2,6-dioxo-4-pyrimidinyl, or 2,5-dioxo-4-imidazolindinyl or

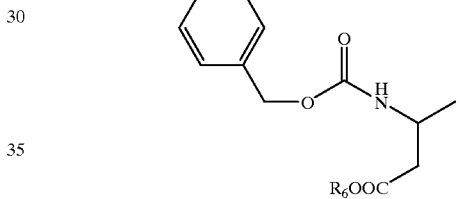

IIc wherein $R_6$ is hydrogen or $C_{1-4}$alkyl;

$R_2$ is indol-3-yl-methyl, $C_{5-7}$arylC$_{1-4}$alkyl, wherein such aryl groups or aryl-moieties or aryl-containing groups are optionally substituted with hydroxy or halo, benzothienylmethyl or $C_{1-4}$alkyl;

$R_3$ is formyl, maleimidomethyl, methoxycarbonylvinyl, dimethoxymethyl, semicarbazonomethyl, $C_{1-4}$alkyl, $R_4$dithio, $R_4$dithio-$C_{1-4}$alkyl, $R_4$dithioacetyl, $R_7C_{1-4}$alkylamido, $R_7C_{1-4}$alkylamidomethyl, —COR$_8$, —CH(OH)R$_9$, —COCOR$_{10}$, or COC≡CR$_{11}$;

wherein $R_4$ is $C_{1-4}$alkyl, $C_{5-7}$aryl, or $C_{1-4}$alkyl, $C_{5-7}$aryl; $R_7$ is acetoxy, halo, maleimido or hydroxy; $R_8$ is

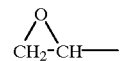

CHO, $C_{1-4}$alkenyl, $C_{1-4}$alkylhalo or $C_{1-4}$alkylthio; $R_9$ is CHO, $C_{1-4}$alkenyl, or

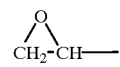

such oxiranyl moiety being optionally substituted with $C_{1-4}$alkyl or $C_{1-4}$alkoxycarbonyl;

$R_{10}$ is $C_{1-4}$alkoxy, $C_{5-7}$aryloxy, $C_{1-4}$alkyl, hydrogen, hydroxy or methoxycarbonyl; and $R_{11}$ is hydrogen or Si(CH$_2$); such aryl groups or aryl moieties or aryl-containing groups being optionally substituted with nitro or carboxy;

X is indol-3-yl-methyl, or bromobenzyl; and

Y is 2-naphthylmethyl or indol-3-yl-methyl.

2. The compound according to claim 1, wherein $R_1$ is $C_{5-7}$aryl$C_{1-4}$alkoxy, $C_{5-7}$aryl$C_{1-4}$alkyl, $C_{5-7}$aryloxy$C_{1-4}$alkyl or is a group of Formula IIa or IIb wherein n=0 or 1 and wherein Z is —CONH— or —CH$_2$— and $R_5$ is benzyloxy or 1,2,3,6-tetrahydro-2,6-dioxo-4-pyrimidinyl or 2,5-dioxo-4-imidazolidinyl or is a group of Formula IIc wherein $R_6$ is hydrogen or $C_{1-4}$alkyl.

3. The compound according to claim 1, wherein $R_2$ is indol-3yl-methyl, or benzyl optionally substituted with halo or hydroxy.

4. The compound according to claim 3, wherein $R_2$ is indol-3-yl methyl, chlorobenzyl, bromobenzyl, benzyl, or 4-hydroxybenzyl.

5. The compound according to claim 4, wherein $R_2$ is indol-3-yl-methyl.

6. The compound according to claim 1, wherein $R_3$ is formyl, semicarbazonomethyl, —COR$_8$, $R_7C_{1-4}$alkylamido or $R_7C_{1-4}$alkylamidomethyl; in which $R_8$ is

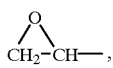

CHO, $C_{1-4}$alkenyl, $C_{1-4}$alkylhalo or $C_{1-4}$alkylthio; and $R_7$ is acetoxy, halo, maleimido, or hydroxy.

7. The compound according to claim 6, wherein $R_3$ is formyl, 2-oxiranylcarbonyl, semicarbazonomethyl, glyoxyloyl, acryloyl, 2-chloroacetyl, 2-acetoxyacetamido, (2-chloro-acetamido)methyl, (2-maleimidoacetamido)-methyl, 3(maleimidoacetamido)-methyl, 1-maleimidomethyl or (3-maleimidopropionamido)methyl.

8. The compound according to claim 7, wherein $R_3$ is formyl, semicarbazonomethyl or 2-oxiranylcarbonyl.

9. The compound according to claim 1, wherein $R_1$ is 5-(hexahydro-2-oxy-1H-thieno[3,4-d]imidazol-4-yl)butyl or benzyloxy; $R_2$ is indol-3-yl-methyl; and $R_3$ is formyl or oxiranylcarbonyl.

10. The compound according to claim 2, wherein $R_1$ is selected from the group consisting of benzyloxy, [5-(hexahydro-2-oxo-1H-thieno[3,4-d]imidazol-4-yl) valeramido]pentyl, 6-[6-(1,2,3,6-tetrahydro-2,6-dioxo-4-pyrimidinyl)formamido]hexanamidopentyl, 6-[6-(benzyloxy)formamido]hexanamidopentyl, 12-[(benzyloxy)acetamido]undecanyl, 5-phenylbutyl, phenoxyethyl, 5-(hexahydro-2-oxo-(1H-thieno[3,4-d]imidazol-4-yl)butyl, 3-pyridylmethoxy, benzyl, 2-phenylethyl, 3-phenylethyl, N-(benzyloxy)carbonyl-4-O-tert-butyl-L-aspart-1-yl, N-(benzyloxy)carbonyl-L-aspart-1-yl, 6-[6-[2-(2,5-dioxo-4-imidazolidinyl)acetamido]hexanamido]pentyl, 3-pyridylmethoxy, and 6-benzyloxycarbonyl-aminopentyl.

11. The compound according to claim 10, wherein $R_1$ is benzyloxy or 5-(hexahydro-2-oxo-1H-thieno[3,4-d] imidazol-4-yl)butyl.

12. A composition comprising a compound or salt thereof according to claim 1, in an amount effective to inhibit endothelin converting enzyme and a carrier.

13. A compound selected from the group consisting of:
N-[[5-(hexahydro-2-oxo-1H-thieno[3,4-d]imidazol-4-yl) pentanoyl]-1-p-bromophenylalanyl-L-1-naphthylalanyl-L-N-[1-formyl]2-(1H-indol-3-yl)ethyl]amide, N-[[5-(hexahydro-2-oxo-1H-thieno[3,4-d]imidazol-4-yl) pentanoyl]-L-tryptophanyl-L-tryptophanyl-L-N-[1-formyl]2-(1H-indol-3-yl)ethyl]amide, N-[(benzyloxy)carbonyl-L-p-bromophenylalanyl-L-1-naphthylalanyl-L-N-[1-[2-oxiranylcarbonyl]]2-phenylethyl]amide, N-[(benzyloxy)carbonyl-L-p-bromophenylalanyl-L-1-naphthylalanyl-1-L-formyl-1-(1H-indol-3-yl-methyl)-methyl]amide, N-[(benzyloxy)carbonyl-L-p-bromophenylalanyl-L-2-naphthylalanyl-1-L-formyl-1-(1H-indol-3-yl-methyl)-methyl]amide, N-[(benzyloxy)carbonyl-L-tryptophanyl-L-1-naphthylalanyl-1-L-formyl-1-(1H-indol-3-yl-methyl)-methyl]amide, and N-[(benzyloxy)carbonyl-L-p-iodophenylalanyl-L-1-naphthylalanyl-1-L-formyl-1-(1H-indol-3-yl-methyl)-methyl]amide;

and salts thereof.

14. A compound selected from the group consisting of:
N-[[5-(hexahydro-2-oxo-1H-thieno[3,4-d]imidazol-4-yl) pentanoyl]-L-p-bromophenylalanyl-L-1-naphthylalanyl-L-N-[1-formyl]2-(1H-indol-3-yl)ethyl] amide, N-[[5-(hexahydro-2-oxo-1H-thieno[3,4-d]imdazol-4-yl) pentanoyl]-L-trypothyanyl-L-tryptophan-L-N-[1-formyl]2-(1H-indol-3-yl)ethyl]amide, N-(benzyloxy)carbonyl-L-p-bromophenylalanyl-L-1-naphthylalanyl-L-N-[1-[2-oxiranylcarbonyl]2-phenylethyl]amide, and N-[(benzyloxy)carbonyl-L-p-bromophenylalanyl-L-1-naphthylalanyl-1-L-formyl-1-(1H-indol-3-yl-methyl)-methyl]amide;

and salts thereof.

15. N-[(benzyloxy)carbonyl-L-p-bromophenylalanyl-L-1-naphthylalanyl-1-L-formyl-1-(1H-indol-3-yl-methyl)-methyl]amide or a salt thereof.

16. N-[(benzyloxy)carbonyl-L-isoleucyl-L-isoleucine-L-N-[1-[2-oxiranylcarbonyl]2-phenylethyl]amide or a salt thereof.

17. A compound of formula III or a salt thereof

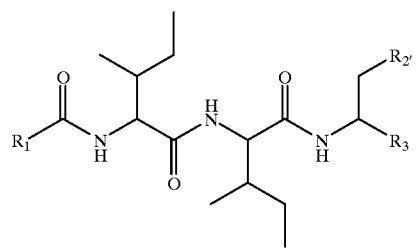

wherein $R_1$ is selected from the group consisting of $C_{5-7}$aryl, $C_{5-7}$aryl$C_{1-4}$alkyl, carboxy$C_{1-4}$alkyl, $C_{1-4}$alkyl and $C_{5-7}$aryl$C_{1-4}$alkoxy, such aryl groups or aryl moieties of aryl-containing groups being optionally substituted with $C_{1-4}$alkyl, halo, nitro, carboxyl or sulphonyl;

$R_{2'}$ is methyl$R_2$ and $R_2$ is selected from the group consisting of indol-3-yl, phenyl, isobutyl and benzothienyl; and $R_3$ is selected from the group consisting of formyl, glyoxyloyl, haloacetyl, $C_{1-4}$alkoxalyl, $C_{5-7}$aryloxalyl, $R_4$dithio, $R_4$dithio$C_{1-4}$alkyl, $R_4$dithioacetyl, $C_{1-4}$alkyl, acryloyl and 2-oxiranylcarbonyl such oxiranyl being optionally substituted with a $C_{1-4}$alkyl or $C_{1-4}$alkoxycarbonyl wherein $R_4$ is selected from the group consisting of $C_{1-4}$alkyl, $C_{5-7}$aryl and $C_{1-4}$alkyl$C_{5-7}$aryl, such aryl groups or aryl moieties of aryl-containing groups being optionally substituted with nitro or carboxyl.

* * * * *